(12) United States Patent
Yamakose et al.

(10) Patent No.: US 9,180,099 B2
(45) Date of Patent: Nov. 10, 2015

(54) PYRROLOQUINOLINYL-PYRROLIDINE-2,5-DIONE FORMULATIONS AND METHODS FOR PREPARING AND USING SAME

(75) Inventors: Hiroshi Yamakose, Kanagawa (JP); Takafumi Kato, Kanagawa (JP)

(73) Assignee: ArQule Inc., Burlington, MA (US)

( * ) Notice: Subject to any disclaimer, the term of this patent is extended or adjusted under 35 U.S.C. 154(b) by 446 days.

(21) Appl. No.: 13/543,007

(22) Filed: Jul. 6, 2012

(65) Prior Publication Data
US 2013/0011481 A1    Jan. 10, 2013

Related U.S. Application Data

(60) Provisional application No. 61/505,175, filed on Jul. 7, 2011.

(51) Int. Cl.
| | |
|---|---|
| *A61K 9/14* | (2006.01) |
| *A61K 31/4745* | (2006.01) |
| *B29B 9/12* | (2006.01) |
| *B32B 5/16* | (2006.01) |
| *A61P 35/00* | (2006.01) |
| *A61K 9/20* | (2006.01) |
| *A61K 31/4725* | (2006.01) |

(52) U.S. Cl.
CPC .............. *A61K 9/2018* (2013.01); *A61K 9/2054* (2013.01); *A61K 9/2095* (2013.01); *A61K 31/4725* (2013.01); *Y10T 428/2982* (2015.01)

(58) Field of Classification Search
CPC . A61K 9/2018; A61K 9/2054; A61K 9/2095; A61K 31/4745; Y10T 428/2982
See application file for complete search history.

(56) References Cited

U.S. PATENT DOCUMENTS

| | | | |
|---|---|---|---|
| 4,522,811 A | 6/1985 | Eppstein et al. | |
| 5,510,118 A * | 4/1996 | Bosch et al. | 424/489 |
| 7,713,969 B2 | 5/2010 | Li et al. | |
| 2004/0258757 A1 | 12/2004 | Bosch et al. | |
| 2007/0178051 A1 | 8/2007 | Pruitt et al. | |
| 2007/0218138 A1 * | 9/2007 | Bittorf et al. | 424/488 |
| 2009/0035366 A1 | 2/2009 | Liversidge et al. | |
| 2010/0016597 A1 | 1/2010 | Hirokawa et al. | |
| 2010/0221251 A1 | 9/2010 | Li et al. | |
| 2010/0297075 A1 | 11/2010 | Chan et al. | |
| 2011/0160242 A1 | 6/2011 | Reed et al. | |

FOREIGN PATENT DOCUMENTS

| | | |
|---|---|---|
| CN | 101636150 | 1/2010 |
| EP | 1897558 | 3/2008 |
| WO | WO 02/00196 | 1/2002 |
| WO | WO-2006086484 A1 | 8/2006 |
| WO | WO-2010093789 A2 | 8/2010 |

OTHER PUBLICATIONS

Mithani, S. D. et al. Estimation of the Increase in Solubility of Drugs as a Function of Bile Salt Concentration, Pharmaceutical Research, 13(1), 1996.*
Shohin, I. E. et al. Evaluation of in Vitro Equivalence for Drugs Containing BCS Class II Compound Ketoprofen, Dissolution Technologies, p. 26-29, Feb. 2011.*
Beviglia et al. "Expression of the c-Met/HGF Receptor in Human Breast Carcinoma: Correlation with Tumor Progression." *Int. J. Cancer. (Pred. Oncol.)* 74.3(1997):301-309.
Danilkovitch-Miagkova et al. "Dysregulation of Met Receptor Tyrosine Kinase Activity in Invasive Tumors." *J. Clin. Invest.* 109(2002):863-867.
Li et al. "Selective Killing of Cancer Cells by β-Lapachone: Direct Checkpoint Activation as a Strategy Against Cancer." *PNAS.* 100. 5(2003):2674-2678.
Ma et al. "c-Met: Structure, Functions and Potential for Therapeutic Inhibition." *Cancer Metastasis Rev.* 22.4(2003):309-325.
Qian et al. "Met Protein Expression Level Correlates with Survival in Patients with Late-Stage Nasopharyngeal Carcinoma." *Cancer Res.* 62.2(2002):589-596.
Qiao et al. "Constitutive Activation of Met Kinase in Non-Small-Cell Lung Carcinomas Correlates with Anchorage-Independent Cell Survival." *J. Cell. Biochem.* 86.4(2002):665-677.
Takeuchi et al. "c-Met Expression Level in Primary Colon Cancer: A Predictor of Tumor Invasion and Lymph Node Metastases." *Clin. Cancer Res.* 9.4(2003):1480-1488.
Thürlimann et al. "Management of Primary Breast Cancer: An Update." *Onkologie.* 27.2(2004):175-179.
Zhang et al. "Met Decoys: Will Cancer Take the Bait?" *Cancer Cell.* 6.1(2004):5-6.

\* cited by examiner

*Primary Examiner* — Johann R Richter
*Assistant Examiner* — Genevieve S Alley
(74) *Attorney, Agent, or Firm* — Cooley LLP; Ivor R. Elrifi; Matthew Pavao

(57) ABSTRACT

The present invention provides pyrroloquinolinyl-pyrrole-2,5-dione formulations and methods of treating a cell proliferative disorder, such as a cancer, by administering to a subject in need thereof a therapeutically effective amount of the formulations containing pyrroloquinolinyl-pyrrole-2,5-dione compounds.

16 Claims, 1 Drawing Sheet

(±)-cis-3-(5,6-dihydro-4H-pyrrolo [3,2,1-ij] quinolin-1yl)-4(1H-indol-3-yl) pyrrolidine-2, 5-dione
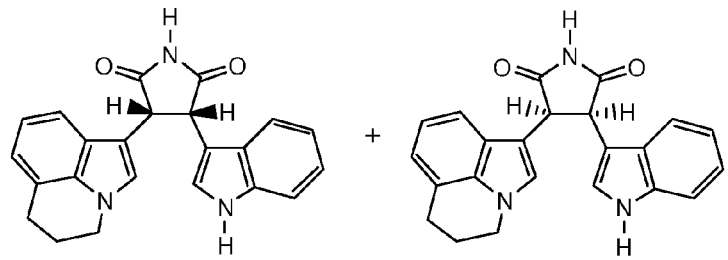
(±)-trans-3-(5,6-dihydro-4H-pyrrolo [3,2,1-ij] quinolin-1-yl)-4(1H-indol-3-yl) pyrrolidine-2, 5-dione.
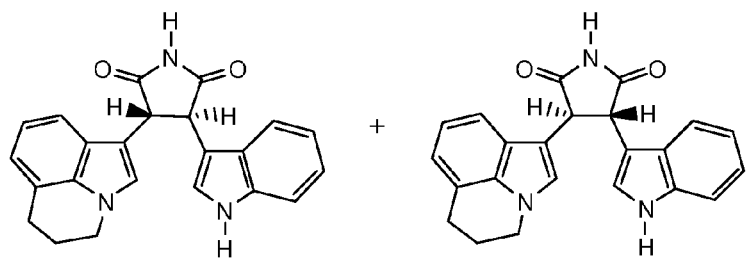

PYRROLOQUINOLINYL-PYRROLIDINE-2,5-DIONE FORMULATIONS AND METHODS FOR PREPARING AND USING SAME

CROSS-REFERENCE TO RELATED APPLICATIONS

This application claims priority to, and the benefit of, U.S. Provisional Application No. 61/505,175, filed Jul. 7, 2011, the contents of which are incorporated herein by reference in their entirety.

BACKGROUND OF THE INVENTION

Cancer is the second leading cause of death in the United States, exceeded only by heart disease. (*Cancer Facts and Figures* 2004, American Cancer Society, Inc.) Despite recent advances in cancer diagnosis and treatment, surgery and radiotherapy may be curative if a cancer is found early, but current drug therapies for metastatic disease are mostly palliative and seldom offer a long-term cure. Even with new chemotherapies entering the market, the need continues for new drugs effective in monotherapy or in combination with existing agents as first line therapy, and as second and third line therapies in treatment of resistant tumors.

Cancer cells are by definition heterogeneous. For example, within a single tissue or cell type, multiple mutational 'mechanisms' may lead to the development of cancer. As such, heterogeneity frequently exists between cancer cells taken from tumors of the same tissue and same histiotype that have originated in different individuals. Frequently observed mutational 'mechanisms' associated with some cancers may differ between one tissue type and another (e.g., frequently observed mutational 'mechanisms' leading to colon cancer may differ from frequently observed 'mechanisms' leading to leukemias). It is therefore often difficult to predict whether a particular cancer will respond to a particular chemotherapeutic agent. (*Cancer Medicine*, 5th Edition, Bast et al. eds., B.C. Decker Inc., Hamilton, Ontario)

Components of cellular signal transduction pathways that regulate the growth and differentiation of normal cells can, when dysregulated, lead to the development of cellular proliferative disorders and cancer. Mutations in cellular signaling proteins may cause such proteins to become expressed or activated at inappropriate levels or at inappropriate times during the cell cycle, which in turn may lead to uncontrolled cellular growth or changes in cell-cell attachment properties. For example, dysregulation of receptor tyrosine kinases by mutation, gene rearrangement, gene amplification, and over-expression of both receptor and ligand has been implicated in the development and progression of human cancers.

The c-Met receptor tyrosine kinase is the only known high-affinity receptor for hepatocyte growth factor (HGF), also known as scatter factor. Binding of HGF to the c-Met extra-cellular ligand-binding domain results in receptor multimerization and phosphorylation of multiple tyrosine residues in the intracellular portion of c-Met. Activation of c-Met results in the binding and phosphorylation of adaptor proteins such as Gab-1, Grb-2, Shc, and c-Cbl, and subsequent activation of signal transducers such as PI3K, PLC-γ, STATs, ERK1 and 2 and FAK. c-Met and HGF are dysregulated in human cancers, and may contribute to dysregulation of cell growth, tumor cell dissemination, and tumor invasion during disease progression and metastasis. (See, e.g., *Journal of Clinical Investigation* 109: 863-867 (2002) and *Cancer Cell* pp 5-6 July 2004) c-Met and HGF are highly expressed relative to surrounding tissue in numerous cancers, and their expression correlates with poor patient prognosis. (See, e.g., *Journal of Cellular Biochemistry* 86: 665-677 (2002); *Int. J. Cancer (Pred. Oncol.)* 74: 301-309 (1997); *Clinical Cancer Research* 9: 1480-1488 (2003); and *Cancer Research* 62: 589-596 (2002)) Without intending to be bound by theory, c-Met and HGF may protect tumors against cell death induced by DNA damaging agents, and as such may contribute to chemoresistance and radioresistance of tumors. Without intending to be limited by any theory, inhibitors of c-Met may be useful as therapeutic agents in the treatment of proliferative disorders including breast cancer. (See, e.g., *Cancer and Metastasis Reviews* 22: 309-325 (2003)). Accordingly, new compounds and methods for modulating these factors and treating cancer are needed. The present invention addresses these needs.

SUMMARY OF THE INVENTION

The present invention provides a composition including a compound having solubility of 0 to 10 µg/mL in water at 37° C. wherein said compound is in the form of crystalline particles wherein 99% of the particles have a diameter of 27 µm or lower.

The present invention also provides a method including mixing a composition including a compound having solubility of 0 to 10 µg/mL in water at 37° C. wherein said compound is in the form of crystalline particles wherein 99% of the particles have a diameter of 27 µm or lower and at least one additive; wet-granulating the obtained mixture with an aqueous solution including a binder; and optionally mixing the obtained granules with a lubricant.

The present invention further provides a method including mixing a composition including a compound having solubility of 0 to 10 µg/mL in water at 37° C. wherein said compound is in the form of crystalline particles wherein 99% of the particles have a diameter of 27 µm or lower and at least one additive; kneading the obtained mixture with an aqueous solution including a binder; extrusion-granulating the kneaded mixture by pressing it against a die or screen surface; and optionally mixing the obtained granules with a lubricant.

In the composition, 90% of the particles can have a diameter of 17 µm or lower, preferably about 4 µm to about 10 µm. In the composition, 50% of the particles have a diameter of 7 µm or lower, preferably about 1 µm to about 4 µm. The composition can be substantially free of surfactant, contain less than 1% surfactant, contain less than 0.5% surfactant, or contain less than 0.1% surfactant.

The compound can have a solubility of 0 to 3.5 µg/mL in water at 37° C. The compound can be a compound of formula III, IIIa, IVa, IVb, Va, or Vb, or a pharmaceutically acceptable salt thereof, or a prodrug or metabolite thereof. Preferably, the compound is (−)-trans-3-(5,6-dihydro-4H-pyrrolo[3,2,1-ij]quinolin-1-yl)-4-(1H-indol-3-yl)pyrrolidine-2,5-dione or a pharmaceutically acceptable salt, prodrug or metabolite thereof.

The composition can include an additive. The additive can be a diluent, disintegrant, binder, lubricant, stabilizer, or corrective. Preferably, the diluent is a sugar derivative, a starch derivative, or a cellulose derivative. More preferably, the diluent is lactose.

The composition can include a coating agent. The coating agent can be a sugar coating base agent, water-soluble film coating base agent, enteric film coating base agent, or sustained-release film coating base agent. The coating agent can include a plasticizer, diluent, lubricant, masking agent, colorant, gloss agent, or antiseptic.

The composition can be a powder, fine granule, granule, capsule, or tablet. Preferably, the composition is a tablet.

The composition includes about 10% to about 60% by weight of the compound. More preferably, about 30% to about 50% by weight.

Wet granulating can be performed using a high shear granulator, fluid bed granulator, rotary granulator, or kneading granulator. Preferably, it is performed using a high shear granulator or a fluid bed granulator.

The methods of the present invention further include drying and or tableting the granules. In some embodiments, the compound and the additive are not co-mixed. In other embodiments, the compound is pulverized prior to being mixed with the additive.

The present invention also provides the granules obtained by the methods provided herein.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

BRIEF DESCRIPTION OF THE FIGURES

FIG. 1 sets forth the chemical structures of (±)-cis-3-(5,6-dihydro-4H-pyrrolo [3,2,1-ij] quinolin-1-yl)-4-(1H-indol-3-yl) pyrrolidine-2, 5-dione and (±)-trans-3-(5,6-dihydro-4H-pyrrolo [3,2,1-ij] quinolin-1-yl)-4-(1H-indol-3-yl) pyrrolidine-2, 5-dione.

DETAILED DESCRIPTION OF THE INVENTION

The Pharmaceutical Compositions and Formulations

Pharmaceutical preparations containing a poorly water-soluble drug require some tools for improving the dissolution property of the drug. For example, pulverizing the drug, adding a surfactant, or amorphizing the drug is known. However, the addition of the surfactant may chemically destabilize the drug. Moreover, depending on the amount of the surfactant, it needs to be adsorbed onto an additive and then added to solid preparations. This may complicate production steps. Alternatively, the method of amorphizing the drug requires changing the crystal form. Thus, any of these tools are not easy.

When compositions containing a high concentration of a poorly water-soluble drug are produced, usually, powders are tableted by direct compression or granules are produced by a dry or wet granulation method and tableted. However, the former approach, in which powder of a pulverized drug is tableted by direct compression, is largely affected by the physical properties of the drug and often has great weight variations at the time of tableting, resulting in poor manufacturability in consideration of productivity. Also, this approach disadvantageously has the inferior dissolution property of the drug. Moreover, even when, in the latter approach, granules are produced by a dry granulation method (e.g., using a roller compactor) using powder of a pulverized drug and the obtained granules are tableted, it is also affected by the physical properties of the drug and may have great weight variations at the time of tableting, resulting in poor manufacturability in consideration of productivity. Also, this approach disadvantageously has the inferior dissolution property of the drug.

The present invention provides a composition including a compound having solubility of 0 to 10 μg/mL in water at 37° C. wherein said compound is in the form of crystalline particles wherein 99% of the particles have a diameter of 27 μm or lower.

The present invention also provides a method including mixing a composition including a compound having solubility of 0 to 10 μg/mL in water at 37° C. wherein said compound is in the form of crystalline particles wherein 99% of the particles have a diameter of 27 μm or lower and at least one additive; wet-granulating the obtained mixture with an aqueous solution including a binder; and optionally mixing the obtained granules with a lubricant.

The present invention further provides a method including mixing a composition including a compound having solubility of 0 to 10 μg/mL in water at 37° C. wherein said compound is in the form of crystalline particles wherein 99% of the particles have a diameter of 27 μm or lower and at least one additive; kneading the obtained mixture with an aqueous solution including a binder; extrusion-granulating the kneaded mixture by pressing it against a die or screen surface; and optionally mixing the obtained granules with a lubricant.

In the composition, 90% of the particles can have a diameter of 17 μm or lower, preferably about 4 μm to about 10 μm. In the composition, 50% of the particles have a diameter of 7 μm or lower, preferably about 1 μm to about 4 μm.

The composition can be substantially free of surfactant, contain less than 1% surfactant, contain less than 0.5% surfactant or contain less than 0.1% surfactant.

The compound can have a solubility of 0 to 3.5 μg/mL in water at 37° C. The compound can be a compound of formula III, IIIa, IVa, IVb, Va, or Vb, or a pharmaceutically acceptable salt thereof, or a prodrug or metabolite thereof. Preferably, the compound is (−)-trans-3-(5,6-dihydro-4H-pyrrolo[3,2,1-ij] quinolin-1-yl)-4-(1H-indol-3-yl)pyrrolidine-2,5-dione or a pharmaceutically acceptable salt, prodrug or metabolite thereof.

The composition can include an additive. The additive can be a diluent, disintegrant, binder, lubricant, stabilizer, or corrective. Preferably, the diluent is a sugar derivative, a starch derivative, or a cellulose derivative. More preferably, the diluent is lactose.

The composition can include a coating agent. The coating agent can be a sugar coating base agent, water-soluble film coating base agent, enteric film coating base agent, or sustained-release film coating base agent. The coating agent can include a plasticizer, diluent, lubricant, masking agent, colorant, gloss agent, or antiseptic.

The composition can be a powder, fine granule, granule, capsule, or tablet. Preferably, the composition is a tablet.

The composition includes about 10% to about 60% by weight of the compound. More preferably, about 30% to about 50% by weight.

Wet granulating can be performed using a high shear granulator, fluid bed granulator, rotary granulator, or kneading granulator. Preferably, it is performed using a high shear granulator or a fluid bed granulator.

The methods of the present invention further include drying and or tableting the granules. In some embodiments, the compound and the additive are not co-mixed. In other embodiments, the compound is pulverized prior to being mixed with the additive.

The present invention also provides the granules obtained by the methods provided herein.

According to the present invention, a tablet that contains a pulverized poorly water-soluble drug and is excellent in manufacturability and the dissolution property of the drug can be produced even though the tablet is free of a surfactant.

A "poorly water-soluble drug" according to the present invention is a drug having solubility of 0 to 10 μg/mL in water at 37° C., preferably a drug having solubility of 0 to 5 μg/mL in water at 37° C., more preferably a drug having solubility of 0 to 3.5 μg/mL in water at 37° C., even more preferably (−)-trans-3-(5,6-dihydro-4H-pyrrolo[3,2,1-ij]quinolin-1-yl)-4-(1H-indol-3-yl)pyrrolidine-2,5-dione or a pharmacologically acceptable salt thereof, most preferably (−)-trans-3-(5,6-dihydro-4H-pyrrolo[3,2,1-ij]quinolin-1-yl)-4-(1H-indol-3-yl)pyrrolidine-2,5-dione.

In the present invention, it is preferred that the poorly water-soluble drug should be pulverized before being mixed with additives. In the present invention, the "pulverization" is carried out for the purpose of crushing solid particles by the application of mechanical force such as impact, compression, shearing, or friction thereto to reduce the particle sizes, thereby facilitating the formation of a homogeneous mixed state and improving the dissolution rate and bioavailability of the drug owing to the increased surface area (which refers to a specific surface area SSA) of the drug. The known pulverizing method includes: high-speed rotating impact mills (hammer mills and impact mills) for obtaining 50% cumulative particle diameter around 10 μm, which perform pulverizing by means of the impact force of a high-speed rotating hammer or pin in a pulverizing chamber; carrier mills (ball mills or vibration mills) which pulverize powder by means of impact force or friction force in a rotating cylinder in which the powder and magnetic balls are placed; and fluid energy mills (jet mills) for obtaining 50% cumulative particle diameter smaller than a few μm, which perform pulverizing by jetting compressed air and raw material particles from a nozzle and colliding the particles accelerated by the jet of air with swirling particles in a pulverizing chamber.

Particles can be measured using the following:

Particle diameter distribution measurement apparatus: HELOS (H1326) & RODOS System (manufactured by Sympatec GmbH);

Measurement range of laser diffraction apparatus: 0.5 to 875 μm;

Calculation mode of laser diffraction apparatus: Fraunhofer HRLD (v3.2 Rel. 2);

Disperser: RODOS, dry dispersion system;

Dispersive pressure: 2.50 bar;

Degree of vacuum: 90.00 mbar.

In particle diameter measured under the conditions described above, the 50% cumulative particle diameter in particle size distribution is preferably 7 μm or smaller, more preferably 1 μm to 7 μm, and further more preferably 1 μm to 4 μm, the 90% cumulative particle diameter in particle size distribution is preferably 17 μm or smaller, more preferably 4 μm to 17 μm, and further more preferably 4 μm to 10 μm, and the 99% cumulative particle diameter in particle size distribution is preferably 27 μm or smaller, more preferably 10 μm to 27 μm, more preferably 9 μm to 27 μm, and further more preferably 9 μm to 15 μm. Furthermore preferably the 50% cumulative particle diameter in particle size distribution is 7 μm or smaller, and the 90% cumulative particle diameter in particle size distribution is 17 μm or smaller, further more preferably the 50% cumulative particle diameter in particle size distribution is 1 μm to 7 μm, and the 90% cumulative particle diameter in particle size distribution is 4 μm to 17 μm, preferably the 50% cumulative particle diameter in particle size distribution is 1 μm to 4 μm, and the 90% cumulative particle diameter in particle size distribution is 4 μm to 10 μm. Especially preferably the 50% cumulative particle diameter in particle size distribution is 1 μm to 7 μm, the 90% cumulative particle diameter in particle size distribution is 4 μm to 17 μm, and the 99% cumulative particle diameter in particle size distribution is 9 μm to 27 μm, and most preferably the 50% cumulative particle diameter in particle size distribution is 1 μm to 4 μm, the 90% cumulative particle diameter in particle size distribution is 4 μm to 10 μm, and the 99% cumulative particle diameter in particle size distribution is 9 μm to 15 μm.

The "additive" according to the present invention is not particularly limited as long as it is an additive used in usual pharmaceutical solid preparations and does not inhibit drug administration. Examples thereof include diluents, disintegrants, binders, lubricants, stabilizers, and correctives.

The diluents used in the present invention can be, for example, organic diluents including: sugar derivatives such as lactose, saccharose, glucose, mannitol, and sorbitol; starch derivatives such as corn starch, potato starch, α-starch, and dextrin; cellulose derivatives such as crystalline cellulose; gum arabic; and dextran, or inorganic diluents including: silicate derivatives such as light anhydrous silicic acid, synthetic aluminum silicate, calcium silicate, and magnesium aluminometasilicate; phosphate such as calcium hydrogen phosphate; carbonate such as calcium carbonate; and sulfate such as calcium sulfate, and is preferably organic diluents, more preferably sugars, even more preferably lactose, most preferably lactose monohydrate.

The disintegrant used in the present invention can be, for example, a cellulose derivative such as low-substituted hydroxypropyl cellulose, carboxymethylcellulose, calcium carboxymethylcellulose, or internally cross-linked sodium carboxymethylcellulose, chemically modified starch/cellulose such as carboxymethyl starch, sodium carboxymethyl starch, cross-linked polyvinyl pyrrolidone, or partially pregelatinized starch, or corn starch and is preferably crosscarmellose sodium.

The binder used in the present invention can be, for example, hydroxypropyl cellulose, hydroxypropyl methylcellulose, polyvinyl pyrrolidone, polyethylene glycol, pregelatinized starch, gelatin, ethylcellulose, or copolyvidone, and is preferably hydroxypropyl cellulose.

The lubricant used in the present invention can be, for example, stearic acid; metal stearate such as calcium stearate or magnesium stearate; talc; colloidal silica; waxes such as beads wax or spermaceti; boric acid; adipic acid; sulfate such as sodium sulfate; glycol; fumaric acid; sodium stearyl fumarate; sucrose fatty acid ester; sodium benzoate; D,L-leucine; lauryl sulfate such as sodium lauryl sulfate or magnesium lauryl sulfate; silicic acids such as silicic anhydride or silicic acid hydrate; or the starch derivatives exemplified above, and is preferably metal stearate, and more preferably magnesium stearate.

The stabilizer used in the present invention can be, for example, p-hydroxybenzoic ester such as methylparaben or propylparaben; alcohols such as chlorobutanol, benzyl alcohol, or phenylethyl alcohol; benzalkonium chloride; phenols such as phenol or cresol; thimerosal; dehydroacetic acid; or sorbic acid.

The correctives used in the present invention can be, for example, a sweetener such as saccharine sodium or aspartame; an acidulant such as citric acid, malic acid, or tartaric acid; a flavor such as menthol, lemon flavor, strawberry flavor, or orange flavor; L-aspartic acid; inosinic acid; licorice; sodium L-glutamate; sodium chloride; or glycyrrhizinic acid.

Coating is performed using, for example, a film coating apparatus. Examples of film coating agents can include sugar coating base agents, water-soluble film coating base agents, enteric film coating base agents, and sustained-release film coating base agents.

Saccharose is used as the sugar coating base agents. Furthermore, one or combination of two or more selected from talc, precipitated calcium carbonate, calcium phosphate, calcium sulfate, gelatin, gum arabic, polyvinyl pyrrolidone, and pullulan, and the like can also be used.

Examples of the water-soluble film coating base agents can include: cellulose derivatives such as hydroxypropyl cellulose, hydroxypropyl methylcellulose, hydroxyethyl cellulose, methyl hydroxyethyl cellulose, and sodium carboxymethyl cellulose; synthetic polymers such as polyvinylacetal diethyl aminoacetate, aminoalkyl methacrylate copolymers, and polyvinylpyrrolidone; and polysaccharides such as pullulan.

Examples of the enteric film coating base agents can include: cellulose derivatives such as hydroxypropyl methylcellulose phthalate, hydroxypropyl methylcellulose acetate succinate, carboxymethyl ethylcellulose, and cellulose acetate phthalate; acrylic acid derivatives such as (meth) acrylic acid copolymer L, (meth)acrylic acid copolymer LD, and (meth)acrylic acid copolymer S; and natural products such as shellac.

Examples of the sustained-release film coating base agents can include: cellulose derivatives such as ethyl cellulose; and acrylic acid derivatives such as aminoalkyl methacrylate copolymer RS and ethyl acrylate/methyl methacrylate copolymer emulsions.

These coating base agents may be used as a mixture at an appropriate ratio of two or more thereof. Moreover, the coating base agents can further optionally contain appropriate pharmacologically acceptable additives such as plasticizers, diluents, lubricants, masking agents, colorants, gloss agents, and/or antiseptics.

The type of the plasticizer that can be used in the present invention is not particularly limited and may be selected appropriately by those skilled in the art. Examples of such plasticizers can include propylene glycol, polyethylene glycol, polypropylene glycol, glycerin and sorbitol, glycerin triacetate, diethyl phthalate and triethyl citrate, lauric acid, sucrose, dextrose, sorbitol, triacetin, acetyl triethyl citrate, triethyl citrate, tributyl citrate, and acetyl tributyl citrate.

Examples of the masking agents that can be used in the present invention can include titanium dioxide.

Examples of the colorants that can be used in the present invention can include titanium dioxide, iron oxide, iron oxide red, iron oxide yellow, and yellow No. 5 aluminum lake talc.

Examples of the gloss agents that can be used in the present invention can include carnauba wax, talc, gelatin, shellacs, and paraffins.

Examples of the antiseptics that can be used in the present invention can include paraben.

Solid preparations comprising the granules of the present invention is also encompassed by the present invention. Examples of such solid preparations can include tablets (including sublingual tablets and orally disintegrating tablets), capsules (including soft capsules and microcapsules), granules, fine granules, powders, pills, chewable tablets, and troches. The solid preparation is preferably a powder, a fine granule, a granule, a capsule, or a tablet, most preferably a tablet.

A method for producing the preparation according to the present invention, the production can be performed using a general method described in publications such as Power Technology and Pharmaceutical Process (D. Chulia et al., Elsevier Science Pub Co (Dec. 1, 1993)) and is particularly preferably a wet production process.

Various wet granulation methods such as high shear granulation, fluid bed granulation, rotary granulation, and kneading granulation methods are known as the wet granulation method according to the present invention. Each method that is considered to be optimal is adopted according to the form of the preparation of interest, the properties of the raw material, etc. Preferably, high shear granulation and fluid bed granulation methods are used, and the high shear granulation method, which is almost free from a loss of contents during granulation, is particularly preferable.

The amount of the poorly water-soluble drug formulated in the granules of the present invention is not particularly limited and is, for example, 10 to 60% by weight, preferably 30 to 50% by weight, with respect to the total weight of the granules.

Moreover, the amount of the additive formulated in the granules of the present invention is not particularly limited. For example, 20 to 80% by weight (preferably 40 to 60% by weight) of the diluents, 2 to 12% by weight (preferably 5 to 10% by weight) of the disintegrant, 1 to 5% by weight (preferably 2 to 3% by weight) of the binder, and 0.5 to 2% by weight (preferably 0.5 to 1.5% by weight) of the lubricant, with respect to the total weight of the granules are preferably formulated.

In the present invention, it is not required that the poorly water-soluble drug and the diluents should be co-pulverized in advance before high shear granulation.

In the present invention, the high shear granulation method is a method as shown below.

The diluents, the disintegrant, the binder, the stabilizer, and a pH adjuster, and the like are added to the drug and mixed by the rotation of stiffing blades and cross screws in a high shear granulator, followed by high shear granulation with a water or a binder solution added. After drying, a size selection is performed to obtain granules. The granules can also be produced using water. The lubricant is added to the obtained granules and blended. Then, the mixture is tableted to obtain a tablet. Moreover, the tablet of the present invention may be provided with at least one layer film coating.

In the present invention, the fluid bed granulation method is a method as shown below.

The diluents and the disintegrant, and the like are added to the drug. The mixture is flowed in an air current in a fluid bed granulator, and a binder solution is sprayed thereto from a nozzle. Agglomeration is promoted by the collision of particles to increase the particle size. After drying, size selection is performed to obtain granules.

The granules according to the present invention is a spherical or indefinite granules of 80 to 220 microns in 50% cumulative particle diameter.

The granulation according to the present invention refers to a procedure of preparing particles with almost uniform shapes and sizes from raw materials in a powder form, a mass form, a solution, or a melted liquid state, or the like, and includes granulation for preparing final products such as granules, powders, or fine granules, and granulation for preparing intermediate products for production of tablets or capsules, or the like. The granules for tableting described later is also encompassed by the granules of the present invention.

In the present invention, the phrase "excellent in manufacturability" refers to small weight variations of obtained tablets without causing problems such as capping, sticking, and lamination in the tableting step even in the large-scale manufacture of the solid preparations, such as production in factories. The weight variations serve as indexes applicable to Uniformity of Dosage Units as the general test method of the Japanese Pharmacopoeia. Assessed values of content uniformity and the maximum allowable acceptance value (L1=15.0) of the assessed values can be used as such indexes.

Examples of indexes for problems in tableting include weight deviation and the physical problems (capping, sticking, and lamination).

In the present invention, a direct compression method for producing a preparation refers to a method which comprises adding the diluent and, if necessary, the binder/disintegrant in a powder form to the drug, adding the lubricant to the prepared mixture, and directly compressing this mixture using a tableting machine to form a tablet.

In the present invention, a dry granulation method for producing a tablet refers to a method which comprises: adding the diluent, the disintegrant, the binder, and the lubricant, and the like to the drug and mixing them; then compression-molding the raw material powder using a tableting machine (slugging method) or a roll compactor (roller compaction method), followed by crushing/breakup by an appropriate method; and formulating a tablet using the produced granules.

In the present invention, the compression molding process is a process of applying pressure to the raw material powder by means of mechanical force to make the raw material powder into a mass. Examples apparatuses used therein can include rotary tableting machines (manufactured by KIKUSUI SEISAKUSHO LTD., HATA IRON WORKS CO., LTD., SUGAWARA SEIKI Co., Ltd., etc.) and dry granulators such as roller compactors, roll granulators, and Chilsonator (manufactured by Freund Corp, TURBO KOGYO CO., LTD., KURIMOTO, LTD., MATSUBO Corp., NIPPON GRANULATOR CO., LTD., Fuji Paudal Co., Ltd., etc.).

In the present invention, the crushing/breakup process is a process of crushing the mass formed in the compression molding process, into an appropriate size using a knife, a cutter, or the like. Examples apparatuses used therein can include cutting mills or screening mills such as power mills, FitzMill, Fiore, and Comil (manufactured by Fuji Paudal Co., Ltd., TOKUJU CO., LTD., Powrex corp., etc.).

In the present invention, a wet granulation method for producing a tablet is a method as shown below.

The wet granulation techniques are broadly classified into: "high shear granulation type" which performs granulation by applying high-energy shearing force and impact force to the raw material powder and the binder by the rotation of stiffing blades and choppers; "extrusion granulation type" which performs granulation by supplying the raw material powder into a rotating screw portion, forcedly moving it forward with compression under pressure, and continuously extruding the compressed product from pores of a die (wire mesh) attached to the tip or side of the screw; "rotary granulation type" which produces spherical particles by spraying the binder to or coating with the binder the rotated raw material powder; and "fluid bed granulation type" which involves flowing the raw material powder in an air current, spraying thereto a binder solution from a nozzle, and promoting agglomeration by the collision of particles to increase the particle size. The "high shear granulation type" includes "vessel-fixed type granulators with stirring blades" that rotate blades at a high speed, such as NMG, High-Speed Mixer, Vertical Granulator, Diosna, New Speed Kneader, Super Mixer, and Henschel Mixer (manufactured by NARA MACHINERY CO., LTD., Fukae powtec, Powrex corp., MUTUAL CORP., OKADA SEIKO CO., LTD., Kawata Corp., Mitsui Mining Co., Ltd., etc.). The "extrusion granulation type" includes basket- or screw-type extrusion granulators such as DomeGran, Basketruzer, and Pellet Extrusion Granulator (manufactured by DALTON CO., LTD., Fuji Paudal Co., Ltd., N.P. Labo Co., Ltd., AKIRAKIKO Co., Ltd., Fukae powtec, etc.). The "rotary granulation type" includes Malmerizer, CF Granulator, etc. (manufactured by Fuji Paudal Co., Ltd., Freund Corp., etc.). The "fluid bed granulation type" includes "fluid bed type" including GLATT or Flow Coater (manufactured by Powrex corp., Freund Corp., etc.), and "rotating fluid bed type" including New Malmerizer, Spiral Flow, SPIRA COTA, Granulex, etc. (manufactured by Fuji Paudal Co., Ltd., DALTON CO., LTD., Freund Corp, OKADA SEIKO CO., LTD., etc.).

The granules thus obtained can be size-screened to have the desired particle diameter and made into preparations in the form of powders, fine granules, or granules. These preparations can also be charged into capsule shells to form capsules. Alternatively, the disintegrant and/or the lubricant, and the like are further added thereto, if necessary, and the mixture can also be compression-molded using a tableting machine or the like to form preparations in the form of tablets. Any of the procedures such as mixing or granulation are generally used in the field of pharmaceutical techniques and can be carried out appropriately by those skilled in the art.

In the present invention, a test is conducted at 50 rpm using 900 mL of a phosphate buffer containing 1% sodium lauryl sulfate (pH 6.8) as a test solution according to the dissolution test method (Apparatus II) described in the paragraph of the Japanese Pharmacopoeia, 15th edition (e.g., each test solution was collected after 5 minutes, 10 minutes, 15 minutes, 30 minutes, 45 minutes, and 60 minutes into the test, and the dissolution rate of the compound was measured by absorbance spectroscopy or high-performance liquid chromatography [an dissolution tester manufactured by Toyama Sangyo Co., Ltd., and a spectrophotometer and high-performance liquid chromatography manufactured by Shimadzu Corp.]; the test was conducted on 6 tablets, and an average of their dissolution rates was calculated; the granules can be evaluated by a similar test method.

In the present invention, the tableting is a process of applying pressure to the raw material powder by means of mechanical force to make the raw material powder into a mass. Examples apparatuses used therein can include rotary tableting machines (manufactured by KIKUSUI SEISAKUSHO LTD., HATA IRON WORKS CO., LTD., SUGAWARA SEIKI Co., Ltd., FETTE COMPACTING GmbH, etc.).

The tablet obtained in the present invention may be a round tablet or a tablet of varying shapes having a surface shape such as normal cup radius surface, radius surface for sugar-coating, flat surface with beveled edge, flat surface with radius, or convex surface with two radius, etc. The size of the tablet is not particularly limited as long as it is the size of a usual pharmaceutical tablet. For the round tablet, the lower limit is a diameter of 5.0 mm, and the upper limit is 9.5 mm. Tablets of as small size as possible are preferable in consideration of manufacturability or dissolution property. The color of the tablet is not particularly limited and may be a white or red-orange color.

The pharmaceutical preparation of the present invention thus produced by various production methods using 3-(5,6-dihydro-4H-pyrrolo[3,2,1-ij]quinolin-1-yl)-4-(1H-indol-3- yl)pyrrolidine-2,5-dione or a pharmacologically acceptable salt thereof and various additives can be stored stably for a long period.

The amount of the coating agent formulated in the tablet of the present invention is not particularly limited and is, for example, 1.7 to 5.4% by weight, preferably 3.5 to 4.6% by weight, with respect to the total weight of the tablet.

Pyrroloquinolinyl-pyrrole-2,5-diones and pyrroloquinolinyl-pyrrolidine-2,5-diones The pyrroloquinolinyl-pyrrole-2,5-dione compounds of formula III and IIIa are:

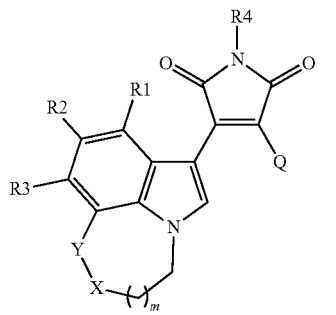

(III)

where:

R1, R2 and R3 are independently selected from the group consisting of hydrogen, F, Cl, Br, I, —NR5R6, —($C_1$-$C_6$) alkyl, —($C_1$-$C_6$) substituted alkyl, —($C_3$-$C_9$)cycloalkyl, —($C_3$-$C_9$) substituted cycloalkyl, —O—($C_1$-$C_6$) alkyl, —O—($C_1$-$C_6$) substituted alkyl, —O—($C_3$-$C_9$) cycloalkyl, —O—($C_3$-$C_9$) substituted cycloalkyl, aryl, heteroaryl, and heterocyclyl;

R4 is selected from the group consisting of hydrogen, —($C_1$-$C_6$) alkyl, and —$CH_2$R7;

R5 and R6 are independently selected from the group consisting of hydrogen and —($C_1$-$C_6$) alkyl;

R7 is selected from the group consisting of —O—P(=O)(OH)$_2$, —O—P(=O)(—OH)(—O—($C_1$-$C_6$) alkyl), —O—P(=O)(—O—($C_1$-$C_6$) alkyl)$_2$, —O—P(=O)(—OH) (—O—($CH_2$)-phenyl), —O—P(=O)(—O—($CH_2$)-phenyl)$_2$, a carboxylic acid group, an amino carboxylic acid group, and a peptide;

Q is selected from the group consisting of aryl, heteroaryl, —O-aryl, —S-aryl, —O-heteroaryl, and —S-heteroaryl;

X is selected from the group consisting of —($CH_2$)—, —(NR8)-, S, and O;

R8 is selected from the group consisting of hydrogen, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —C(=O)—O—($C_1$-$C_6$) alkyl, and —C(=O)—O—($C_1$-$C_6$) substituted alkyl;

Y is selected from the group consisting of —($CH_2$)— or a bond; and m is 1 or 2, wherein said aryl, heteroaryl, —O-aryl, —S-aryl, —O-heteroaryl, and —S-heteroaryl groups may be substituted with one or more substituents independently selected from the group consisting of F, Cl, Br, I, —NR5R6, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —O—($C_1$-$C_6$) substituted alkyl, —O—($C_3$-$C_9$) cycloalkyl, —O—($C_3$-$C_9$) substituted cycloalkyl, -aryl, -aryl-($C_1$-$C_6$) alkyl, -aryl-($C_1$-$C_6$) alkyl, —O-aryl, —O—($C_1$-$C_4$) alkyl aryl, heteroaryl, heterocyclyl, —O—($C_1$-$C_4$) alkyl heterocycle, and —(S(=O)$_2$)—($C_1$-$C_6$) alkyl.

For the compound of formula IIIa, Q is selected from the group consisting of aryl, heteroaryl, —O-aryl, —S-aryl, —O-heteroaryl, and —S-heteroaryl, provided that when R4 is hydrogen, or ($C_1$-$C_4$) alkyl, Q is not 3-indolyl or substituted 3-indolyl.

The pyrroloquinolinyl-pyrrolidine-2,5-dione compounds of formula IVa, IVb, Va, or Vb, are:

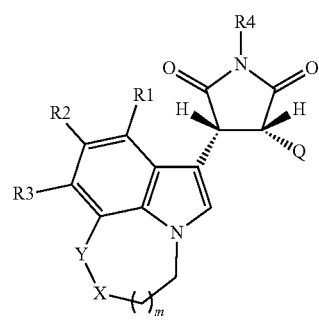

(IVa)

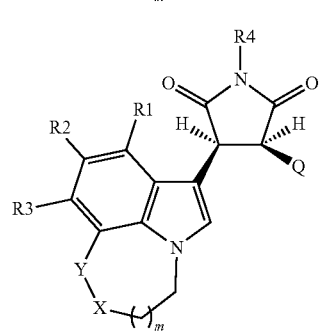

(IVb)

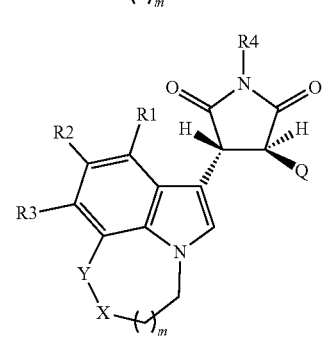

(Va)

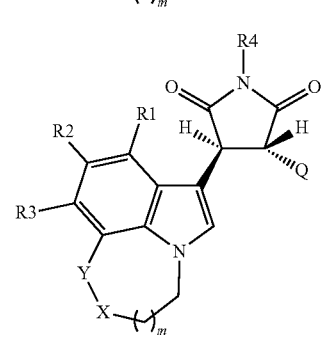

(Vb)

where:

R1, R2 and R3 are independently selected from the group consisting of hydrogen, F, Cl, Br, I, —NR5R6, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —O—($C_1$-$C_6$) substituted alkyl, —O—($C_3$-$C_9$) cycloalkyl, —O—($C_3$-$C_9$) substituted cycloalkyl, aryl, heteroaryl, and heterocyclyl;

R4 is selected from the group consisting of hydrogen, —($C_1$-$C_6$) alkyl, and —$CH_2$R7;

R5 and R6 are independently selected from the group consisting of hydrogen and —($C_1$-$C_6$) alkyl;

R7 is selected from the group consisting of —O—P(=O)(OH)$_2$, —O—P(=O)(—OH)(—O—($C_1$-$C_6$) alkyl), —O—P(=O)(—O—($C_1$-$C_6$) alkyl)$_2$, —O—P(=O)(—OH)(—O—($CH_2$)-phenyl), —O—P(=O)(—O—($CH_2$)-phenyl)$_2$, a carboxylic acid group, an amino carboxylic acid group, and a peptide;

Q is selected from the group consisting of aryl, heteroaryl, —O-aryl, —S-aryl, —O-heteroaryl, and —S-heteroaryl;

X is selected from the group consisting of —($CH_2$)—, —(NR8)-, S, and O;

R8 is selected from the group consisting of hydrogen, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —C(=O)—O—($C_1$-$C_6$) alkyl, and —C(=O)—O—($C_1$-$C_6$) substituted alkyl;

Y is selected from the group consisting of —($CH_2$)— and a bond;

m is 1 or 2, wherein said aryl, heteroaryl, —O-aryl, —S-aryly, —O-heteroaryl, and —S-heteroaryl groups may be substituted with one or more substituents independently selected from the group consisting of F, Cl, Br, I, —NR5R6, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —O—($C_1$-$C_6$) substituted alkyl, —O—($C_3$-$C_9$) cycloalkyl, —O—($C_3$-$C_9$) substituted cycloalkyl, -aryl, -aryl-($C_1$-$C_6$) alkyl, -aryl-($C_1$-$C_6$) alkyl, —O-aryl, —O—($C_1$-$C_4$) alkyl aryl, heteroaryl, heterocyclyl, —O—($C_1$-$C_4$) alkyl heterocycle, and —(S(=O)$_2$)—($C_1$-$C_6$) alkyl.

The preparation of a compound of formula III, IIIa, IVa, IVb, Va or Vb is described in WO 2010/093789 and US 20100297075, the entire contents of which are incorporated herein by reference.

Definitions

The term "alkyl" refers to radicals containing carbon and hydrogen, without unsaturation. Alkyl radicals can be straight or branched. Exemplary alkyl radicals include, without limitation, methyl, ethyl, propyl, isopropyl, hexyl, t-butyl, sec-butyl and the like. Acyl groups may be denoted by a range, thus, for example, a ($C_1$-$C_6$) alkyl group is an alkyl group having from one to six carbon atoms in the straight or branched alkyl backbone. Substituted and unsubstituted alkyl groups may independently be ($C_1$-$C_5$) alkyl, ($C_1$-$C_6$) alkyl, ($C_1$-$C_{10}$) alkyl, ($C_3$-$C_{10}$) alkyl, or ($C_5$-$C_{10}$) alkyl. Unless expressly stated, the term "alkyl" does not include "cycloalkyl."

A "cycloalkyl" group refers to a cyclic alkyl group having the indicated number of carbon atoms in the "ring portion," where the "ring portion" may consist of one or more ring structures either as fused, spiro, or bridged ring structures. For example, a C3 to C6 cycloalkyl group (e.g., ($C_3$-$C_6$) cycloalkyl) is a ring structure having between 3 and 6 carbon atoms in the ring. When no range is given, then cycloalkyl has between three and nine carbon atoms (($C_3$-$C_9$) cycloalkyl) in the ring portion. Exemplary cycloalkyl groups include, but are not limited to cyclopropyl, cyclobutyl, cyclopentyl, cyclohexyl, cycloheptyl, and adamantyl. Preferred cycloalkyl groups have three, four, five, six, seven, eight, nine, or from three to nine carbon atoms in the ring structure.

The term substituted alkyl and substituted cycloalkyl, refer to alkyl and cycloalkyl groups, as defined above, substituted with one or more substituents independently selected from the group consisting of fluorine, aryl, heteroaryl, —O—($C_1$-$C_6$) alkyl, and —NR5R6, where R5 and R6 are independently selected from the group consisting of hydrogen and —($C_1$-$C_6$) alkyl.

The term "aryl" refers to an aromatic carbocyclic group, having one, two, or three aromatic rings. Exemplary aryl groups include, without limitation, phenyl, naphthyl, and the like. Aryl groups include one, two, or three aromatic rings structures fused with one or more additional nonromantic carbocyclic or heterocyclic rings having from 4-9 members. Examples of fused aryl groups include benzocyclobutene, indanyl, tetrahydronapthylenyl, 1,2,3,4-tetrahydrophenanthrenyl, tetrahydroanthracenyl, 1,4-dihydro-1,4-methanonaphthalenyl, benzodioxolyl.

The term "heteroaryl" refers to a heteroaromatic (heteroaryl) group having one, two, or three aromatic rings containing from 1-4 heteroatoms (such as nitrogen, sulfur, or oxygen) in the aromatic ring. Heteroaryl groups include one, two, or three aromatic rings structures containing from 1-4 heteroatoms fused with one or more additional nonaromatic rings having from 4-9 members. Heteroaryl groups containing a single type of heteroatom in the aromatic ring are denoted by the type of hetero atom they contain, thus, nitrogen-containing heteroaryl, oxygen-containing heteroaryl and sulfur-containing heteroaryl denote heteroaromatic groups containing one or more nitrogen, oxygen or sulfur atoms respectively. Exemplary heteroaryl groups include, without limitation, pyridyl, pyrimidinyl, triazolyl, quinolyl, quinazolinyl, thiazolyl, benzo[b]thiophenyl, furanyl, imidazolyl, indolyl, and the like.

The terms "heterocyclyl" or "heterocycle" refers to either saturated or unsaturated, stable non-aromatic ring structures that may be fused, spiro or bridged to form additional rings. Each heterocycle consists of one or more carbon atoms and from one to four heteroatoms selected from the group consisting of nitrogen, oxygen and sulfur. "Heterocyclyl" or "heterocycle" include stable non-aromatic 3-7 membered monocyclic heterocyclic ring structures and 8-11 membered bicyclic heterocyclic ring structures. A heterocyclyl radical may be attached at any endocyclic carbon or nitrogen atom that results in the creation of a stable structure. Preferred heterocycles include 3-7 membered monocyclic heterocycles (more preferably 5-7-membered monocyclic heterocycles) and 8-10 membered bicyclic heterocycles. Examples of such groups include piperidinyl, piperazinyl, pyranyl, pyrrolidinyl, morpholinyl, thiomorpholinyl, oxopiperidinyl, oxopyrrolidinyl, oxoazepinyl, azepinyl, isoxozolyl, tetrahydropyranyl, tetrahydrofuranyl, dioxolyl, dioxinyl, oxathiolyl, dithiolyl, sulfolanyl, dioxanyl, dioxolanyl, tetrahydrofurodihydrofuranyl, tetrahydropyranodihydro-furanyl, dihydropyranyl, tetrahydrofurofuranyl, tetrahydropyranofuran, quinuclidinyl (1-azabicyclo[2.2.2]octanyl) and tropanyl (8-methyl-8-azabicyclo[3.2.1]octanyl).

For the purpose of the Q substituent, the term "substituted 3-indolyl" refers to a 3-indolyl group substituted with one or more substituents selected from the group consisting of: F, Cl, Br, I, —NR5R6, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —O—($C_1$-$C_6$) substituted alkyl, —O—($C_3$-$C_9$) cycloalkyl, —O—($C_3$-$C_9$) substituted cycloalkyl, -aryl, -aryl-($C_1$-$C_6$) alkyl, -aryl-O—($C_1$-$C_6$) alkyl, —O-aryl, —O—($C_1$-$C_4$) alkyl-aryl, heteroaryl, heterocyclyl, —O—($C_1$-$C_4$) alkyl-heterocycle, and —(S(=O)$_2$)—

($C_1$-$C_6$) alkyl; where R5, R6 are independently selected from the group consisting of hydrogen, and —($C_1$-$C_6$) alkyl.

For the purposes of the R7 substituent, the term "carboxylic acid group" refers to a group of the form —O—C(=O)—($C_1$-$C_6$) alkyl, —O—C(=O)—($C_3$-$C_9$) cycloalkyl, —O—C(=O)-aryl, —O—C(=O)-heteroaryl, —O—C(=O)-heterocycle, —O—C(=O)—($C_1$-$C_6$) alkyl-aryl, —O—C(=O)—($C_1$-$C_6$) alkyl-heteroaryl, or —O—C(=O)—($C_1$-$C_6$) alkyl-heterocycle. Included in "carboxylic acid group" are groups of the form —O—C(=O)—($C_1$-$C_6$) alkyl, —O—C(=O)—($C_3$-$C_9$) cycloalkyl, —O—C(=O)-aryl, —O—C(=O)-heteroaryl, —O—C(=O)-heterocycle, —O—C(=O)—($C_1$-$C_6$) alkyl-aryl, —O—C(=O)—($C_1$-$C_6$) alkyl-heteroaryl, or —O—C(=O)—($C_1$-$C_6$) alkyl-heterocycle substituted with one or more substituent independently selected from the group consisting of: F, Cl, Br, I, —OH, —SH, —NR5R6, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —O—($C_1$-$C_6$) substituted alkyl, —S—($C_1$-$C_6$) alkyl, —O—($C_3$-$C_9$) cycloalkyl, —O—($C_3$-$C_9$) substituted cycloalkyl, -aryl, —O-aryl, —O—($C_1$-$C_4$) alkyl-aryl, heteroaryl, heterocyclyl, —O—($C_1$-$C_4$) alkyl-heterocycle, —(S(=O)$_2$)—($C_1$-$C_6$) alkyl, —NH—C(=NH)—NH$_2$ (i.e., guanido), —COOH, and —C(=O)—NR5R6, where R5 and R6 are independently selected from the group consisting of hydrogen, and —($C_1$-$C_6$) alkyl. In addition, for the purposes of the R7 substituent the term "amino carboxylic acid group" refers to a carboxylic acid group, including carboxylic acid groups substituted with one or more of the above-stated substituents, which bears one or more independently selected amino groups of the form —NR5R6 where R5 and R6 are independently selected from the group consisting of hydrogen and ($C_1$-$C_6$) alkyl. In one embodiment of this invention, R7 is an alpha amino or imino acid, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine or stereoisomers or racemic mixtures thereof. In another embodiment the of the invention, R7 is alpha amino or imino acid selected from the group consisting of L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and L-valine.

For the purposes of the R7 substituent, the term "peptide" refers to a dipeptide, tripeptide, tetrapeptide or pentapeptide, which release two, three, four, or five amino or imino acids (e.g., proline) respectively upon hydrolysis. For the purpose of R7, peptides are linked to the remainder of the molecule through an ester linkage. In one embodiment, peptides of R7 are comprised of alpha amino or imino acid, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine or stereoisomers or racemic mixtures thereof; and in a more preferred version of this embodiment, the carboxyl group involved in the ester linkage is the carboxyl terminal COOH group of the peptide, as opposed to a side chain carboxyl. In another embodiment the of the invention, R7 is alpha amino or imino acid selected from the group consisting of L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and L-valine; and in a more preferred version of this preferred embodiment, the carboxyl group involved in the ester linkage is the carboxyl terminal COOH group of the peptide, as opposed to a side chain carboxyl.

Preferred Compounds

Included in the preferred embodiments are compounds of formula III, IIIa, IVa, IVb, Va, or Vb, wherein Q is selected from the group consisting of aryl, heteroaryl, —O-aryl, —S-aryl, —O-heteroaryl, and —S-heteroaryl, provided that Q is not 3-indolyl or a substituted 3-indolyl. In other preferred embodiments Q is selected from the group consisting of aryl, heteroaryl, —O-aryl, —S-aryl, —O-heteroaryl, and —S-heteroaryl, provided that when R4 is hydrogen, cycloalkyl, or alkyl, Q is not 3-indolyl or a substituted 3-indolyl. In still other preferred embodiments Q is selected from the group consisting of aryl, heteroaryl, —O-aryl, —S-aryl, —O-heteroaryl, and —S-heteroaryl, provided that when R4 is hydrogen, ($C_3$-$C_4$) cycloalkyl, or ($C_1$-$C_4$) alkyl, Q is not 3-indolyl or substituted 3-indolyl. In another preferred embodiment Q is 3-indolyl or a substituted 3-indolyl provided that R4 is not hydrogen, cycloalkyl, or alkyl. In still another preferred embodiment Q is 3-indolyl or a substituted 3-indolyl provided that R4 is not hydrogen, ($C_3$-$C_4$) cycloalkyl, or ($C_1$-$C_4$) alkyl.

Other preferred embodiments include compounds of formula III, IIIa, IVa, IVb, Va, or Vb where R4 is —CH$_2$R7. These compounds may serve as prodrug forms of the corresponding compounds of formula III, IIIa, IVa, IVb, Va, or Vb where R4 is H. The prodrug form is cleaved by hydrolysis to release the corresponding compound where R4 is H. The hydrolysis may occur by enzymatic or nonenzymatic routes that produce the corresponding hydroxymethylene derivative, which upon subsequent hydrolysis, result in the release of compounds where R4 is H. In one such preferred embodiment R4 is —CH$_2$R7, where R7 is —O—P(=O)(OH)$_2$, —O—P(=O)(—OH)(—O—($C_1$-$C_6$)alkyl), or —O—P(=O)(—O—($C_1$-$C_6$)alkyl)$_2$. In one embodiment where R7 is —O—P(=O)(—O—($C_1$-$C_6$)alkyl)$_2$, the alkyl groups are independently selected. In another preferred embodiment, R4 is —CH$_2$R7, where R7 is a carboxylic acid group or an amino carboxylic acid group. In still another preferred embodiment R7 is a peptide; where in a more preferred embodiment the peptide is linked through an ester bond formed with the carboxyl terminal COOH group of the peptide chain to the remainder of the compound. In other preferred separate and independent embodiments of compounds of formula III, IIIa, IVa, IVb, Va, or Vb where R4 is —CH$_2$R7 and R7 is a peptide, the peptide may be a dipeptide, a tripeptide, a tetrapeptide or a pentapeptide. Preferred amino acid compositions for peptides of the R7 functionality are described above.

Embodiments of compounds of formula III, IIIa, IVa, IVb, Va, or Vb include those where X is selected from the group consisting of —(NR8)-, S, and O, where R8 is independently selected from the group consisting of hydrogen, —($C_1$-$C_6$) alkyl, —($C_1$-$C_6$) substituted alkyl, —($C_3$-$C_9$) cycloalkyl, —($C_3$-$C_9$) substituted cycloalkyl, and —O—($C_1$-$C_6$) alkyl. Other embodiments of compounds of formula III, IIIa, IVa, IVb, Va, or Vb include those where X is —CH$_2$—. In other embodiments of compounds of formula III, IIIa, IVa, IVb, Va, or Vb, X is oxygen (O). In other embodiments of compounds of formula III, IIIa, IVa, IVb, Va, or Vb, X is sulfur (S). In still other embodiments of compounds of formula III, IIIa, IVa, IVb, Va, or Vb, X is —(NR8)-, where R8 is independently selected from the group consisting of hydrogen, —($C_1$-$C_6$) alkyl, —($C_1$-$C_6$) substituted alkyl, —($C_3$-$C_9$) cycloalkyl, —($C_3$-$C_9$) substituted cycloalkyl, and —O—($C_1$-$C_6$) alkyl.

Other preferred embodiments of the invention include compounds of formula III or IIIa, where Q is a heteroaryl or an optionally substituted heteroaryl group. In four separate alternative preferred embodiments of compounds of formula III or IIIa, Q is an optionally substituted monocyclic heteroaryl group, an optionally substituted bicyclic heteroaryl group, an optionally substituted bicyclic heteroaryl group with the proviso that the bicyclic heteroaryl group is not an indolyl group or a substituted indolyl, or an optionally substituted tricyclic heteroaryl group. Optional substituents, when present, are independently selected from those recited for aryl, heteroaryl, —O-aryl, —S-aryl, —O-heteroaryl, and —S-heteroaryl.

Included in the preferred embodiments of the invention are compounds of formula IVa, IVb, Va, or Vb, where Q is a heteroaryl or an optionally substituted heteroaryl group. In four separate alternative preferred embodiments of compounds of formula IVa, IVb, Va, or Vb, Q is an optionally substituted monocyclic heteroaryl group, an optionally substituted bicyclic heteroaryl group, an optionally substituted bicyclic heteroaryl group with the proviso that the bicyclic heteroaryl group is not indolyl, or an optionally substituted tricyclic heteroaryl group. In a more preferred embodiment, Q is an optionally substituted nitrogen-containing heteroaryl group. In a related embodiment, Q is an optionally substituted indolyl. Optional substituents, when present are independently selected from those recited for aryl, heteroaryl, —O-aryl, —S-aryl, —O-heteroaryl, and —S-heteroaryl.

Preferred embodiments of the invention include mixtures of compounds of formula IVa and IVb, including racemic mixtures. In another preferred embodiment, the compounds of formula IVa and IVb are the separate enantiomers of (±)-cis-3-(5,6-dihydro-4H-pyrrolo[3,2,1-ij] quinolin-1-yl)-4-(1H-indol-3-yl) pyrrolidine-2,5-dione.

Compounds of the invention can be prepared according to the synthetic schemes described in WO 2006/086484, U.S. Pat. No. 7,713,969, and US 20100221251, each of which is incorporated by reference in its entirety for all purposes. Briefly, the preparation of (±)-cis-3-(5,6-dihydro-4H-pyrrolo [3,2,1-ij] quinolin-1-yl)-4-(1H-indol-3-yl) pyrrolidine-2,5-dione is prepared as a mixture beginning with the starting materials 1,2,3,4-tetrahydroquinoline and indole-3-acetamide. The 1,2,3,4-tetrahydroquinoline is converted to 5,6-dihydro-4H-pyrrolo [3,2,1-ij] quinolin-1-yl) oxoacetic acid methyl ester as described in Example 1, steps 1-5 of WO2006/086484, U.S. Pat. No. 7,713,969, and US 20100221251. The 5,6-dihydro-4H-pyrrolo [3,2,1-ij] quinolin-1-yl) oxoacetic acid methyl ester is reacted with indole-3-acetamide as described in Example 1, step 6 of WO2006/086484, U.S. Pat. No. 7,713,969, and US 20100221251, to yield 3-(5,6-dihydro-4H-pyrrolo [3,2,1-ij] quinolin-1-yl)-4-(1H-indol-3-yl) pyrrole-2,5-dione. The mixture of (±)-cis-3-(5,6-dihydro-4H-pyrrolo [3,2,1-ij] quinolin-1-yl)-4-(1H-indol-3-yl) pyrrolidine-2,5-dione is then prepared by catalytic hydrogenation as described in Example 2 using Procedure B of WO2006/086484, U.S. Pat. No. 7,713,969, and US 20100221251.

Preferred embodiments of the invention also include mixtures of compounds of formula Va and Vb, including racemic mixtures. In another preferred embodiment, the compounds of Va and Vb are the separate enantiomers of (±)-trans-3-(5,6-dihydro-4H-pyrrolo [3,2,1-ij] quinolin-1-yl)-4-(1H-indol-3-yl) pyrrolidine-2,5-dione. In this embodiment, the compounds are prepared as a mixture by first preparing (±)-cis-3-(5,6-dihydro-4H-pyrrolo [3,2,1-ij] quinolin-1-yl)-4-(1H-indol-3-yl) pyrrolidine-2, 5-dione, as described above. The mixture of cis compounds is then treated with a mixture of potassium tert-butoxide in tert-butanol to obtain a mixture of (±)-trans-3-(5,6-dihydro-4H-pyrrolo [3,2,1-ij] quinolin-1-yl)-4-(1H-indol-3-yl) pyrrolidine-2, 5-dione as described in Example 3 of WO2006/086484, U.S. Pat. No. 7,713,969, and US 20100221251.

All stereoisomers of the compounds of the instant invention are contemplated, either in admixture or in pure or substantially pure form, including crystalline forms of racemic mixtures and crystalline forms of individual isomers. The definition of the compounds according to the invention embraces all possible stereoisomers (e.g., the R and S configurations for each asymmetric center) and their mixtures. It very particularly embraces the racemic forms and the isolated optical isomers having a specified activity. The racemic forms can be resolved by physical methods, such as, for example, fractional crystallization, separation or crystallization of diastereomeric derivatives, separation by chiral column chromatography or supercritical fluid chromatography. The individual optical isomers can be obtained from the racemates by conventional methods, such as, for example, salt formation with an optically active acid followed by crystallization. Furthermore, all geometric isomers, such as E- and Z-configurations at a double bond, are within the scope of the invention unless otherwise stated. Certain compounds of this invention may exist in tautomeric forms. All such tautomeric forms of the compounds are considered to be within the scope of this invention unless otherwise stated. The present invention also includes one or more regioisomeric mixtures of an analog or derivative.

As used herein, the term "salt" is a pharmaceutically acceptable salt and can include acid addition salts including hydrochlorides, hydrobromides, phosphates, sulphates, hydrogen sulphates, alkylsulphonates, arylsulphonates, acetates, benzoates, citrates, maleates, fumarates, succinates, lactates, and tartrates; alkali metal cations such as $Na^+$, $K^+$, $Li^+$, alkali earth metal salts such as Mg or Ca, or organic amine salts.

As used herein, the term "metabolite" means a product of metabolism of a compound of formula III, IIIa, IVa, IVb, Va, or Vb, or a pharmaceutically acceptable salt, analog or derivative thereof, that exhibits a similar activity in vivo to said a compound of formula III, IIIa, IVa, IVb, Va, or Vb.

As used herein, the term "prodrug" means a compound of formula III, IIIa, IVa, IVb, Va, or Vb covalently linked to one or more pro-moieties, such as an amino acid moiety or other water solubilizing moiety. A compound of formula III, IIIa, IVa, IVb, Va, or Vb may be released from the pro-moiety via hydrolytic, oxidative, and/or enzymatic release mechanisms. In an embodiment, a prodrug composition of the present invention exhibits the added benefit of increased aqueous solubility, improved stability, and improved pharmacokinetic profiles. The pro-moiety may be selected to obtain desired prodrug characteristics. For example, the pro-moiety, e.g., an amino acid moiety or other water solubilizing moiety such as phosphate within R4, may be selected based on solubility, stability, bioavailability, and/or in vivo delivery or uptake.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount," as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with additives and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; a diluent such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one aspect, the active compounds are prepared with pharmaceutically acceptable carriers that will protect the compound against rapid elimination from the body, such as a controlled release formulation, including implants and microencapsulated delivery systems.

Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 3000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

(−)-trans-3-(5,6-dihydro-4H-pyrrolo [3,2,1-ij] quinolin-1-yl)-4-(1H-indol-3-yl) pyrrolidine-2,5-dione is administered at dosage of 360 mg, twice a day, for a maximal daily dosage of 720 mg. Alternatively, (−)-trans-3-(5,6-dihydro-4H-pyrrolo [3,2,1-ij] quinolin-1-yl)-4-(1H-indol-3-yl) pyrrolidine-2, 5-dione is administered at dosage of 240 mg, twice a day, for a maximal daily dosage of 480 mg. (−)-trans-3-(5,6-dihydro-4H-pyrrolo [3,2,1-ij] quinolin-1-yl)-4-(1H-indol-3-yl) pyrrolidine-2, 5-dione is optionally administered to subjects or patients at an initial dosage of 10 mg twice daily for a maximal daily dose of 20 mg, with dosage escalation to administration of 360 mg twice daily for a maximal daily dosage of 720 mg. Preferred dosage forms of (−)-trans-3-(5, 6-dihydro-4H-pyrrolo [3,2,1-ij] quinolin-1-yl)-4-(1H-indol-3-yl) pyrrolidine-2, 5-dione include, but are not limited to, caplets, tablets, pills, and freeze-dried powder. For instance, a subject or patient is administered one 360 mg caplet twice a day, or alternatively, two 180 mg caplets, twice a day, for a maximal daily dosage of 720 mg. (−)-trans-3-(5,6-dihydro-4H-pyrrolo [3,2,1-ij] quinolin-1-yl)-4-(1H-indol-3-yl) pyrrolidine-2,5-dione caplets or tablets are also formulated in 60 mg doses.

The pharmaceutical compositions can include co-formulations of any of the compounds described herein.

The pharmaceutical compositions can be included in a container, pack, or dispenser together with instructions for administration.

Methods of Treatment

The present invention provides methods for the treatment of a cell proliferative disorder in a subject in need thereof by administering to a subject in need of such treatment, a therapeutically effective amount of a compound, composition or formulation of the present invention, or a pharmaceutically acceptable salt, prodrug, metabolite, polymorph or solvate thereof. The cell proliferative disorder can be cancer or a precancerous condition. The present invention further provides the use of a compound of the present invention, or a pharmaceutically acceptable salt, prodrug, metabolite, polymorph or solvate thereof, for the preparation of a medicament useful for the treatment of a cell proliferative disorder.

The present invention also provides methods of protecting against a cell proliferative disorder in a subject in need thereof by administering a therapeutically effective amount of compound of the present invention, or a pharmaceutically acceptable salt, prodrug, metabolite, polymorph or solvate thereof, to a subject in need of such treatment. The cell proliferative disorder can be cancer or a precancerous condition. The present invention also provides the use of compound of the present invention, or a pharmaceutically acceptable salt, prodrug, metabolite, polymorph or solvate thereof, for the preparation of a medicament useful for the prevention of a cell proliferative disorder.

As used herein, a "subject in need thereof" is a subject having a cell proliferative disorder, or a subject having an increased risk of developing a cell proliferative disorder relative to the population at large. A subject in need thereof can have a precancerous condition. Preferably, a subject in need thereof has cancer. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. Preferably, compositions of the present invention may be used to treat a cancer selected from the group consisting of a hematologic cancer of the present invention or a hematologic cell proliferative disorder of the present invention. A hematologic cancer of the present invention can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung. Preferably, compositions of the present invention may be used to treat lung cancer or cell proliferative disorders of the lung. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma", bronchioalveolar carcinoma, giant cell carcinoma, spindle cell carcinoma, and large cell neuroendocrine carcinoma. Lung cancer can include lung neoplasms having histologic and ultrastructual heterogeneity (e.g., mixed cell types).

Cell proliferative disorders of the lung can include all forms of cell proliferative disorders affecting lung cells. Cell proliferative disorders of the lung can include lung cancer, precancerous conditions of the lung. Cell proliferative disorders of the lung can include hyperplasia, metaplasia, and dysplasia of the lung. Cell proliferative disorders of the lung can include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that may predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. Preferably, the cell proliferative disorder of the colon is colon cancer. Preferably, compositions of the present invention may be used to treat colon cancer or cell proliferative disorders of the colon. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary non-polyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

Cell proliferative disorders of the colon can include all forms of cell proliferative disorders affecting colon cells. Cell proliferative disorders of the colon can include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that may predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the pancreas" is a cell proliferative disorder involving cells of the pancreas. Cell proliferative disorders of the pancreas can include all forms of cell proliferative disorders affecting pancreatic cells. Cell proliferative disorders of the pancreas can include pancreas cancer, a precancer or precancerous condition of the pancreas, hyperplasia of the pancreas, and dysaplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructual heterogeneity (e.g., mixed cell types).

A "cell proliferative disorder of the prostate" is a cell proliferative disorder involving cells of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin. Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin.

A "cell proliferative disorder of the ovary" is a cell proliferative disorder involving cells of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

A cell proliferative disorder of the breast can be a precancerous condition of the breast. Compositions of the present invention may be used to treat a precancerous condition of the breast. A precancerous condition of the breast can include atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). A precancerous condition of the breast can be staged according to the TNM classification scheme as accepted by the American Joint Committee on Cancer (AJCC), where the primary tumor (T) has been assigned a stage of T0 or Tis; and where the regional lymph nodes (N) have been assigned a stage of N0; and where distant metastasis (M) has been assigned a stage of M0.

The cell proliferative disorder of the breast can be breast cancer. Preferably, compositions of the present invention may be used to treat breast cancer. Breast cancer includes all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructual heterogeneity (e.g., mixed cell types).

Preferably, compound of the present invention, or a pharmaceutically acceptable salt, prodrug, metabolite, polymorph or solvate thereof, may be used to treat breast cancer. A breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject. A breast cancer that is to be treated can arise in a subject equal to or older than 30 years old, or a subject younger than 30 years old. A breast cancer that is to be treated has arisen in a subject equal to or older than 50 years old, or a subject younger than 50 years old. A breast cancer that is to be treated can arise in a subject equal to or older than 70 years old, or a subject younger than 70 years old.

A breast cancer that is to be treated can be typed to identify a familial or spontaneous mutation in BRCA1, BRCA2, or p53. A breast cancer that is to be treated can be typed as having a HER2/neu gene amplification, as overexpressing HER2/neu, or as having a low, intermediate or high level of HER2/neu expression. A breast cancer that is to be treated can be typed for a marker selected from the group consisting of estrogen receptor (ER), progesterone receptor (PR), human epidermal growth factor receptor-2, Ki-67, CA15-3, CA 27-29, and c-Met. A breast cancer that is to be treated can be typed as ER-unknown, ER-rich or ER-poor. A breast cancer that is to be treated can be typed as ER-negative or ER-positive. ER-typing of a breast cancer may be performed by any reproducible means. ER-typing of a breast cancer may be performed as set forth in Onkologie 27: 175-179 (2004). A breast cancer that is to be treated can be typed as PR-unknown, PR-rich or PR-poor. A breast cancer that is to be treated can be typed as PR-negative or PR-positive. A breast cancer that is to be treated can be typed as receptor positive or receptor negative. A breast cancer that is to be treated can be typed as being associated with elevated blood levels of CA 15-3, or CA 27-29, or both.

A breast cancer that is to be treated can include a localized tumor of the breast. A breast cancer that is to be treated can include a tumor of the breast that is associated with a negative sentinel lymph node (SLN) biopsy. A breast cancer that is to be treated can include a tumor of the breast that is associated with a positive sentinel lymph node (SLN) biopsy. A breast cancer that is to be treated can include a tumor of the breast that is associated with one or more positive axillary lymph nodes, where the axillary lymph nodes have been staged by any applicable method. A breast cancer that is to be treated can include a tumor of the breast that has been typed as having nodal negative status (e.g., node-negative) or nodal positive status (e.g., node-positive). A breast cancer that is to be treated can include a tumor of the breast that has metastasized to other locations in the body. A breast cancer that is to be treated can be classified as having metastasized to a location selected from the group consisting of bone, lung, liver, or brain. A breast cancer that is to be treated can be classified according to a characteristic selected from the group consisting of metastatic, localized, regional, local-regional, locally advanced, distant, multicentric, bilateral, ipsilateral, contralateral, newly diagnosed, recurrent, and inoperable.

A compound of the present invention, or a pharmaceutically acceptable salt, prodrug, metabolite, polymorph or solvate thereof, may be used to treat or prevent a cell proliferative disorder of the breast, or to treat or prevent breast cancer, in a subject having an increased risk of developing breast cancer relative to the population at large. A subject with an increased risk of developing breast cancer relative to the population at large is a female subject with a family history or personal history of breast cancer. A subject with an increased risk of developing breast cancer relative to the population at large is a female subject having a germ-line or spontaneous mutation in BRCA1 or BRCA2, or both. A subject with an increased risk of developing breast cancer relative to the population at large is a female subject with a family history of breast cancer and a germ-line or spontaneous mutation in BRCA1 or BRCA2, or both. A subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. A subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

A breast cancer that is to be treated can histologically graded according to the Scarff-Bloom-Richardson system, wherein a breast tumor has been assigned a mitosis count score of 1, 2, or 3; a nuclear pleiomorphism score of 1, 2, or 3; a tubule formation score of 1, 2, or 3; and a total Scarff-Bloom-Richardson score of between 3 and 9. A breast cancer that is to be treated can be assigned a tumor grade according to the International Consensus Panel on the Treatment of Breast Cancer selected from the group consisting of grade 1, grade 1-2, grade 2, grade 2-3, or grade 3.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present invention, or a pharmaceutically acceptable salt, prodrug, metabolite, polymorph or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present invention, or a pharmaceutically acceptable salt, prodrug, metabolite, polymorph or solvate thereof. The biological or medical response can be the treatment of cancer. The biological or medical response can be treatment or prevention of a cell proliferative disorder. In vitro or in vivo biological assays can include, but are not limited to, enzymatic activity assays, electrophoretic mobility shift assays, reporter gene assays, in vitro cell viability assays, and the assays described herein.

As used herein, "monotherapy" refers to the administration of a single active or therapeutic compound to a subject in need thereof. Preferably, monotherapy will involve administration of a therapeutically effective amount of an active compound. For example, cancer monotherapy with one of the compound of the present invention, or a pharmaceutically acceptable salt, prodrug, metabolite, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, monotherapy with a compound of the present invention, or a pharmaceutically acceptable salt, prodrug, metabolite, polymorph or solvate thereof, is more effective than combination therapy in inducing a desired biological effect.

As used herein, "treating" or "treat" describes the management and care of a patient for the purpose of combating a disease, condition, or disorder and includes the administration of a compound of the present invention, or a pharmaceutically acceptable salt, prodrug, metabolite, polymorph or solvate thereof, to alleviate the symptoms or complications of a disease, condition or disorder, or to eliminate the disease, condition or disorder.

A compound of the present invention, or a pharmaceutically acceptable salt, prodrug, metabolite, polymorph or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute). Furthermore, severity describes a nuclear grade, which refers to the size and shape of the nucleus in tumor cells and the percentage of tumor cells that are dividing (see, National Cancer Institute).

In another aspect of the invention, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

As a cancer grows, it begins to push on nearby organs, blood vessels, and nerves. This pressure creates some of the signs and symptoms of cancer. If the cancer is in a critical area, such as certain parts of the brain, even the smallest tumor can cause early symptoms.

But sometimes cancers start in places where it does not cause any symptoms until the cancer has grown quite large. Pancreas cancers, for example, do not usually grow large enough to be felt from the outside of the body. Some pancreatic cancers do not cause symptoms until they begin to grow around nearby nerves (this causes a backache). Others grow around the bile duct, which blocks the flow of bile and leads to a yellowing of the skin known as jaundice. By the time a pancreatic cancer causes these signs or symptoms, it has usually reached an advanced stage.

A cancer may also cause symptoms such as fever, fatigue, or weight loss. This may be because cancer cells use up much of the body's energy supply or release substances that change the body's metabolism. Or the cancer may cause the immune system to react in ways that produce these symptoms.

Sometimes, cancer cells release substances into the bloodstream that cause symptoms not usually thought to result from cancers. For example, some cancers of the pancreas can release substances which cause blood clots to develop in veins of the legs. Some lung cancers make hormone-like substances that affect blood calcium levels, affecting nerves and muscles and causing weakness and dizziness Cancer presents several general signs or symptoms that occur when a variety of subtypes of cancer cells are present. Most people with cancer will lose weight at some time with their disease. An unexplained (unintentional) weight loss of 10 pounds or more may be the first sign of cancer, particularly cancers of the pancreas, stomach, esophagus, or lung.

Fever is very common with cancer, but is more often seen in advanced disease. Almost all patients with cancer will have fever at some time, especially if the cancer or its treatment affects the immune system and makes it harder for the body to fight infection. Less often, fever may be an early sign of cancer, such as with leukemia or lymphoma.

Fatigue may be an important symptom as cancer progresses. It may happen early, though, in cancers such as with leukemia, or if the cancer is causing an ongoing loss of blood, as in some colon or stomach cancers.

Pain may be an early symptom with some cancers such as bone cancers or testicular cancer. But most often pain is a symptom of advanced disease.

Along with cancers of the skin (see next section), some internal cancers can cause skin signs that can be seen. These changes include the skin looking darker (hyperpigmentation), yellow (jaundice), or red (erythema); itching; or excessive hair growth.

Alternatively, or in addition, cancer subtypes present specific signs or symptoms. Changes in bowel habits or bladder function could indicate cancer. Long-term constipation, diarrhea, or a change in the size of the stool may be a sign of colon cancer. Pain with urination, blood in the urine, or a change in bladder function (such as more frequent or less frequent urination) could be related to bladder or prostate cancer.

Changes in skin condition or appearance of a new skin condition could indicate cancer. Skin cancers may bleed and look like sores that do not heal. A long-lasting sore in the mouth could be an oral cancer, especially in patients who smoke, chew tobacco, or frequently drink alcohol. Sores on the penis or vagina may either be signs of infection or an early cancer.

Unusual bleeding or discharge could indicate cancer. Unusual bleeding can happen in either early or advanced cancer. Blood in the sputum (phlegm) may be a sign of lung cancer. Blood in the stool (or a dark or black stool) could be a sign of colon or rectal cancer. Cancer of the cervix or the endometrium (lining of the uterus) can cause vaginal bleeding. Blood in the urine may be a sign of bladder or kidney cancer. A bloody discharge from the nipple may be a sign of breast cancer.

A thickening or lump in the breast or in other parts of the body could indicate the presence of a cancer. Many cancers can be felt through the skin, mostly in the breast, testicle, lymph nodes (glands), and the soft tissues of the body. A lump or thickening may be an early or late sign of cancer. Any lump or thickening could be indicative of cancer, especially if the formation is new or has grown in size.

Indigestion or trouble swallowing could indicate cancer. While these symptoms commonly have other causes, indigestion or swallowing problems may be a sign of cancer of the esophagus, stomach, or pharynx (throat).

Recent changes in a wart or mole could be indicative of cancer. Any wart, mole, or freckle that changes in color, size, or shape, or loses its definite borders indicates the potential development of cancer. For example, the skin lesion may be a melanoma.

A persistent cough or hoarseness could be indicative of cancer. A cough that does not go away may be a sign of lung cancer. Hoarseness can be a sign of cancer of the larynx (voice box) or thyroid.

While the signs and symptoms listed above are the more common ones seen with cancer, there are many others that are less common and are not listed here. However, all art-recognized signs and symptoms of cancer are contemplated and encompassed by the instant invention.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. Preferably, a compound of the present invention, or a pharmaceutically acceptable salt, prodrug, metabolite, polymorph or solvate thereof, acts selectively on a cancer or precancerous cell but not on a normal cell. Preferably, a compound of the present invention, or a pharmaceutically acceptable salt, prodrug, metabolite, polymorph or solvate thereof, acts selectively to modulate one molecular target (e.g., a target kinase) but does not significantly modulate another molecular target (e.g., a non-target kinase). The invention also provides a method for selectively inhibiting the activity of an enzyme, such as a kinase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A compound of the present invention, or a pharmaceutically acceptable salt, prodrug, metabolite, polymorph or solvate thereof, can modulate the activity of a molecular target (e.g., a target kinase). Modulating refers to stimulating or inhibiting an activity of a molecular target. Preferably, a compound of the present invention, or a pharmaceutically acceptable salt, prodrug, metabolite, polymorph or solvate thereof, modulates the activity of a molecular target if it stimulates or inhibits the activity of the molecular target by at least 2-fold relative to the activity of the molecular target under the same conditions but lacking only the presence of said compound. More preferably, a compound of the present invention, or a pharmaceutically acceptable salt, prodrug, metabolite, polymorph or solvate thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A compound of the present invention, or a pharmaceutically acceptable salt, prodrug, metabolite, polymorph or solvate thereof, does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a kinase isozyme alpha in comparison to a kinase isozyme beta). Preferably, a compound of the present invention, or a pharmaceutically acceptable salt, prodrug, metabolite, polymorph or solvate thereof, demonstrates a minimum of a four fold differential, preferably a ten fold differential, more preferably a fifty fold differential, in the dosage required to achieve a biological effect. Preferably, a compound of the present invention, or a pharmaceutically acceptable salt, prodrug, metabolite, polymorph or solvate thereof, demonstrates this differential across the range of inhibition, and the differential is exemplified at the $IC_{50}$, i.e., a 50% inhibition, for a molecular target of interest.

Administering a compound of the present invention, or a pharmaceutically acceptable salt, prodrug, metabolite, polymorph or solvate thereof, to a cell or a subject in need thereof can result in modulation (i.e., stimulation or inhibition) of an activity of a kinase of interest.

The present invention provides methods to assess biological activity of a compound of the present invention, or a pharmaceutically acceptable salt, prodrug, metabolite, polymorph or solvate thereof. In one method, an assay based on enzymatic activity can be utilized. In one specific enzymatic activity assay, the enzymatic activity is from a kinase. As used herein, "kinase" refers to a large class of enzymes which catalyze the transfer of the γ-phosphate from ATP to the hydroxyl group on the side chain of Ser/Thr or Tyr in proteins and peptides and are intimately involved in the control of various important cell functions, perhaps most notably: signal transduction, differentiation, and proliferation. There are estimated to be about 2,000 distinct protein kinases in the human body, and although each of these phosphorylates particular protein/peptide substrates, they all bind the same second substrate ATP in a highly conserved pocket. About 50% of the known oncogene products are protein tyrosine kinases (PTKs), and their kinase activity has been shown to lead to cell transformation. Preferably, the kinase assayed is a tyrosine kinase.

A change in enzymatic activity caused by a compound of the present invention, or a pharmaceutically acceptable salt, prodrug, metabolite, polymorph or solvate thereof, can be measured in the disclosed assays. The change in enzymatic activity can be characterized by the change in the extent of phosphorylation of certain substrates. As used herein, "phosphorylation" refers to the addition of phosphate groups to a substrate, including proteins and organic molecules; and, plays an important role in regulating the biological activities of proteins. Preferably, the phosphorylation assayed and measured involves the addition of phosphate groups to tyrosine residues. The substrate can be a peptide or protein.

In some assays, immunological reagents, e.g., antibodies and antigens, are employed.

Fluorescence can be utilized in the measurement of enzymatic activity in some assays. As used herein, "fluorescence" refers to a process through which a molecule emits a photon as a result of absorbing an incoming photon of higher energy by the same molecule. Specific methods for assessing the biological activity of the disclosed compounds are described in the examples.

As used herein, an activity of c-Met refers to any biological function or activity that is carried out by c-Met. For example, a function of c-Met includes phosphorylation of downstream target proteins. Other functions of c-Met include autophosphorylation, binding of adaptor proteins such as Gab-1, Grb-2, Shc, SHP2 and c-Cbl, and activation of signal transducers such as Ras, Src, PI3K, PLC-γ, STATs, ERK1 and 2 and FAK.

Administering a compound of the present invention, or a pharmaceutically acceptable salt, prodrug, metabolite, polymorph or solvate thereof, to a cell or a subject in need thereof results in modulation (i.e., stimulation or inhibition) of an activity of an intracellular target (e.g., substrate). Several intracellular targets can be modulated with the compounds of the present invention, including, but not limited to, adaptor proteins such as Gab-1, Grb-2, Shc, SHP2 and c-Cbl, and signal transducers such as Ras, Src, PI3K, PLC-γ, STATs, ERK1 and 2 and FAK.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. A cell cycle checkpoint regulator can be a protein or not a protein.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA*. 100(5): 2674-8, 2003. In an aspect, cell death occurs by apoptosis.

Preferably, an effective amount of a compound of the present invention, or a pharmaceutically acceptable salt, prodrug, metabolite, polymorph or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a compound of the present invention, or a pharmaceutically acceptable salt, prodrug, metabolite, polymorph or solvate thereof, can induce or activate cell death selectively in cancer cells. Administering to a subject in need thereof a compound of the present invention, or a pharmaceutically acceptable salt, prodrug, metabolite, polymorph or solvate thereof, can induce or activate cell death selectively in cancer cells. Contacting a cell with a compound of the present invention, or a pharmaceutically acceptable salt, prodrug, metabolite, polymorph or solvate thereof, can induce cell death selectively in one or more cells affected by a cell proliferative disorder. Preferably, administering to a subject in need thereof a compound of the present invention, or a pharmaceutically acceptable salt, prodrug, metabolite, polymorph or solvate thereof, induces cell death selectively in one or more cells affected by a cell proliferative disorder.

The present invention relates to a method of treating or preventing cancer by administering a compound of the present invention, or a pharmaceutically acceptable salt, prodrug, metabolite, polymorph or solvate thereof, to a subject in need thereof, where administration of the compound of the present invention, or a pharmaceutically acceptable salt, prodrug, metabolite, polymorph or solvate thereof, results in one or more of the following: accumulation of cells in G1 and/or S phase of the cell cycle, cytotoxicity via cell death in cancer cells without a significant amount of cell death in normal cells, antitumor activity in animals with a therapeutic index of at least 2, and activation of a cell cycle checkpoint. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., $18^{th}$ edition (1990). These texts can, of course, also be referred to in making or using an aspect of the invention As used herein, "combination therapy" or "co-therapy" includes the administration of a compound of the present invention, or a pharmaceutically acceptable salt, prodrug, metabolite, polymorph or solvate thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A compound of the present invention, or a pharmaceutically acceptable salt, prodrug, metabolite, analog or derivative thereof, may be administered in combination with a second chemotherapeutic agent. The second chemotherapeutic agent (also referred to as an anti-neoplastic agent or anti-proliferative agent) can be an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase inhibitor), a cytidine analogue drug or any chemotherapeutic, anti-neoplastic or anti-proliferative agent.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine[131] tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus (Torisel); rapamune, ridaforolimus; or AP23573.

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803;SF1126; VX-680; Azd1152; Arry-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur—0.4 M 5-chloro-2,4-dihydroxypyrimidine—1 M potassium oxonate) or lovastatin.

In another aspect, the second chemotherapeutic agent can be a cytokine such as G-CSF (granulocyte colony stimulating factor). In another aspect, a compound of the present invention, or a pharmaceutically acceptable salt, prodrug, metabolite, analog or derivative thereof, may be administered in combination with radiation therapy. Radiation therapy can also be administered in combination with a compound of the present invention and another chemotherapeutic agent described herein as part of a multiple agent therapy. In yet another aspect, a compound of the present invention, or a pharmaceutically acceptable salt, prodrug, metabolite, analog or derivative thereof, may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™) or CMFP (cyclophosphamide, methotrexate, 5-fluorouracil and prednisone).

In preferred embodiments, a compound of the present invention, or a pharmaceutically acceptable salt, prodrug, metabolite, polymorph or solvate thereof, may be administered with an inhibitor of an enzyme, such as a receptor or non-receptor kinase. Receptor and non-receptor kinases of the invention are, for example, tyrosine kinases or serine/threonine kinases. Kinase inhibitors of the invention are small molecules, polynucleic acids, polypeptides, or antibodies.

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-β, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTOR/FRAP1), Eril/Fasudil hydrochloride (targets RHO), Flavopiridol (targets CDK), Seliciclib/CYC202/Roscovitrine (targets CDK), SNS-032/BMS-387032 (targets CDK), Ruboxistaurin (targets PKC), Pkc412 (targets PKC), Bryostatin (targets PKC), KAI-9803 (targets PKC), SF1126 (targets PI3K), VX-680 (targets Aurora kinase), Azd1152 (targets Aurora kinase), Arry-142886/AZD-6244 (targets MAP/MEK), SCIO-469 (targets MAP/MEK), GW681323 (targets MAP/MEK), CC-401 (targets JNK), CEP-1347 (targets JNK), and PD 332991 (targets CDK).

EXAMPLES

Examples are provided below to further illustrate different features of the present invention. The examples also illustrate useful methodology for practicing the invention. These examples do not limit the claimed invention.

Examples of preparation of a compound of formula III, IIIa, IVa, IVb, Va or Vb (including (+)-cis-3-(5,6-dihydro-4H-pyrrolo [3,2,1-ij] quinolin-1-yl)-4-(1H-indol-3-yl)pyrrolidine-2, 5-dione, (−)-cis-3-(5,6-dihydro-4H-pyrrolo [3,2,1-ij] quinolin-1-yl)-4-(1H-indol-3-yl) pyrrolidine-2, 5-dione, (+)-trans-3-(5,6-dihydro-4H-pyrrolo [3,2,1-ij] quinolin-1-yl)-4-(1H-indol-3-yl) pyrrolidine-2, 5-dione, and (−)-trans-3-(5,6-dihydro-4H-pyrrolo [3,2,1-ij] quinolin-1-yl)-4-(1H-indol-3-yl) pyrrolidine-2, 5-dione) and use thereof, either alone or in combination with a therapeutically effective amount of a second anti-proliferative agent, are described in WO2006/086484, U.S. Pat. No. 7,713,969, and US 20100221251, each of which is incorporated by reference in its entirety for all purposes.

Example 1

Wet Granulation 3-(5,6-dihydro-4H-pyrrolo[3,2,1-ij]quinolin-1-yl)-4-(1H-indol-3-yl)pyrrolidine-2,5-dione (796.7 g) pulverized to have a particle size of 1.9 µm in terms of 50% cumulative particle diameter and 5.5 µm in terms of 90% cumulative particle diameter, lactose monohydrate (832.4 g), crosscarmellose sodium (127.4 g), and hydroxypropyl cellulose (45.5 g) were mixed for 3 minutes using a high shear granulator VG-10 (manufactured by Powrex corp.) under conditions involving the number of revolutions of a blade: 250 rpm and the number of revolutions of a chopper: 3000 rpm. After further addition of purified water (981.5 g), the mixture was kneaded for 3 minutes under conditions involving 250 rpm and the number of revolutions of the chopper: 3000 rpm to obtain crude granules. These were granulated using a screen mill Comil QC-194 (manufactured by Powrex corp.) and dried using a fluid bed granulator Flow Coater NFLO-5/2SJ (manufactured by Freund Corp.) under conditions involving an aeration temperature of 90° C. until the product temperature became 55° C. Size-screening was performed using a screen mill Comil QC-194 (manufactured by Powrex corp.) to obtain granules. The obtained granules were blended with magnesium stearate (18.2 g) using a V-blender TVC (5 L) (manufactured by TOKUJU CO., LTD.) to obtain granules for tableting Tablets The granules for tableting obtained in the paragraph (1) were tableted using a tableting machine VEL5 0312SW2MZ (manufactured by KIKUSUI SEISAKUSHO LTD.) at a tableting pressure of 10 kN to obtain core tablets having a tablet weight of 280 mg. To the obtained core tablets, a coating solution comprising hydroxypropyl methylcellulose, titanium dioxide, talc, and iron oxide red was sprayed in a coating machine HCT-Labo (manufactured by Freund Corp.) for film coating to obtain the title tablets. The obtained tablets were subjected to a dissolution test. The test results are shown in Table 2

Example 2

Wet Granulation 3-(5,6-dihydro-4H-pyrrolo[3,2,1-ij]quinolin-1-yl)-4-(1H-indol-3-yl)pyrrolidine-2,5-dione (306 g) pulverized to have a particle size of 1.8 µm in terms of 50% cumulative particle diameter and 6.1 µm in terms of 90% cumulative particle diameter, lactose monohydrate (311.6 g), and crosscarmellose sodium (71.4 g) were mixed for 3 minutes using a high shear granulator VG-5 (manufactured by Powrex corp.) under conditions involving the number of revolutions of a blade: 580 rpm and the number of revolutions of a chopper: 3000 rpm.

After addition of an aqueous hydroxypropyl cellulose solution (357.1 g), the mixture was kneaded for 6 minutes under conditions involving 280 rpm and the number of revolutions of the chopper: 3000 rpm to obtain crude granules. These were dried using a fluid bed granulator Flow Coater NFLO-5/2SJ (manufactured by Freund Corp.) under conditions involving an aeration temperature of 90° C. until the product temperature became 55° C. Size screening was performed using a screen mill Comil QC-U10 (manufactured by Powrex corp.) to obtain granules. The obtained granules were blended with magnesium stearate (5.9 g) using a V-blender S-3-S (manufactured by TOKUJU CO., LTD) to obtain granules for tableting.

Tablets

The granules for tableting obtained in the paragraph (1) were tableted using a rotary tableting machine VEL5 0312SW2MZ (manufactured by KIKUSUI SEISAKUSHO LTD.) at a tableting pressure of 18 kN to obtain core tablets having a tablet weight of 420 mg. To the obtained core tablets, a coating solution comprising hydroxypropyl methylcellulose, titanium dioxide, talc, and iron oxide red was sprayed in a coating machine HCT-Labo (manufactured by Freund Corp.) for film coating to obtain the title tablets. The obtained tablets were subjected to a dissolution test. The test results are shown in Table 2

Comparative Example 1

Direct Compression Method 3-(5,6-dihydro-4H-pyrrolo[3,2,1-ij]quinolin-1-yl)-4-(1H-indol-3-yl)pyrrolidine-2,5-dione (450 g) pulverized to have a particle size of 1.8 μm in terms of 50% cumulative particle diameter and 6.1 μm in terms of 90% cumulative particle diameter, D-mannitol (537.0 g), and crosscarmellose sodium (52.5 g) were premixed for 15 minutes using a V-blender and then sieved using a screen mill Comil QC-U10 (manufactured by Powrex corp.). After addition of magnesium stearate (10.5 g), the mixture was mixed again for 15 minutes in a V-blender to obtain mixed powders.

The obtained mixed powders were tableted using a rotary tableting machine VEL5 0312SW2MZ (manufactured by KIKUSUI SEISAKUSHO LTD.) at a tableting pressure of 18 kN to obtain core tablets having a tablet weight of 420 mg. To the obtained core tablets, a coating solution comprising hydroxypropyl methylcellulose, titanium dioxide, talc, and iron oxide red was sprayed in a coating machine HCT-Labo (manufactured by Freund Corp.) for film coating to obtain the title tablets. The obtained tablets were subjected to a dissolution test. The test results are shown in Table 2

Comparative Example 2

Dry Granulation Method 3-(5,6-dihydro-4H-pyrrolo[3,2,1-ij]quinolin-1-yl)-4-(1H-indol-3-yl)pyrrolidine-2,5-dione (720 g) pulverized to have a particle size of 1.8 μm in terms of 50% cumulative particle diameter and 6.1 μm in terms of 90% cumulative particle diameter, lactose monohydrate (589.0 g), a crystalline cellulose/light anhydrous silicic acid mixture (252.2 g), crosscarmellose sodium (84.0 g), and sodium lauryl sulfate (18.0 g) were premixed for 15 minutes in a V-blender and then sieved using a screen mill Comil QC-U10 (manufactured by Powrex corp.). After addition of magnesium stearate (16.6 g), the mixture was mixed again for 15 minutes in a V-blender to obtain mixed powders.

The obtained mixed powders were tableted using a rotary tableting machine Vergo 0524SS1AX (manufactured by KIKUSUI SEISAKUSHO LTD.) at a tableting pressure of 8 to 30 kN to obtain slug tablets having a tablet weight of 420 mg. The obtained slug tablets were size-screened using a screen mill Comil QC-U10 (manufactured by Powrex corp.) to obtain granules for tableting.

The obtained granules for tableting were tableted using a rotary tableting machine VEL5 0312SW2MZ (manufactured by KIKUSUI SEISAKUSHO LTD.) at a tableting pressure of 18 kN to obtain core tablets having a tablet weight of 420 mg. To the obtained core tablets, a coating solution comprising hydroxypropyl methylcellulose, titanium dioxide, talc, and iron oxide red was sprayed in a coating machine HCT-Labo (manufactured by Freund Corp.) for film coating to obtain the title tablets. The obtained tablets were subjected to a dissolution test. The test results are shown in Table 2

Test Example 1

The yield of the tableting step in Examples 1 and 2 and Comparative Examples 1 and 2 and the weight deviation of the obtained tablets are described in Table 1 below. In this context, the yield of tableting refers to the proportion of the amount of granules for tableting or mixed powders actually used in tablet production, to the expected amount (theoretical value) of granules for tableting or mixed powders when the whole granules for tableting or mixed powders are used in tablets.

TABLE 1

| Production method | Example 1 | Example 2 | Comparative Example 1 | Comparative Example 2 |
|---|---|---|---|---|
| Yield of tableting (%) | 77.9 | 77.4 | 43.5 | 46.1 |
| Weight deviation | 0.8 | 1.0 | 10.2 | 3.8 |

As is evident from Table 1, the preparations of Examples 1 and 2 obtained by the high shear granulation method have more excellent manufacturability than that of the preparations of Comparative Examples 1 and 2 obtained by the direct compression and dry granulation methods Test Example 2

Dissolution Test Method

A test was conducted at 50 rpm using 900 mL of a phosphate buffer containing 1% sodium lauryl sulfate (pH 6.8) as a test solution according to the dissolution test method (apparatus II) described in the paragraph of the Japanese Pharmacopoeia, 15th edition. Each test solution was collected after 15 minutes, 30 minutes, 45 minutes, and 60 minutes into the test, and the dissolution rate of the 3-(5,6-dihydro-4H-pyrrolo[3,2,1-ij]quinolin-1-yl)-4-(1H-indol-3-yl)pyrrolidine-2,5-dione was measured by absorbance spectroscopy [a dissolution tester manufactured by Toyama Sangyo Co., Ltd. and a spectrophotometer manufactured by Shimadzu Corp.]. The test was conducted on 6 tablets, and an average of their dissolution rates was calculated. The dissolution test results are described in Table 2.

TABLE 2

| Dissolution time (min) | Example 1 Dissolution rate (%) | Example 2 Dissolution rate (%) | Comparative Example 1 Dissolution rate (%) | Comparative Example 2 Dissolution rate (%) |
|---|---|---|---|---|
| 15 | 84.3 | 79.5 | 45.7 | 57.9 |
| 30 | 97.0 | 92.7 | 64.5 | 77.2 |
| 45 | 99.9 | 96.5 | 75.6 | 85.4 |
| 60 | 100.8 | 98.1 | 82.7 | 89.9 |

As is evident from Table 2, the preparations of Examples 1 and 2 obtained by the high shear granulation method have more excellent elution property than that of the preparations of Comparative Examples 1 and 2 obtained by the direct compression and dry granulation methods.

What is claimed is:

1. A tablet composition comprising a compound having solubility of 0 to 10 μg/mL in water at 37° C. and less than 0.5% surfactant, wherein the compound is in the form of crystalline particles and wherein 99% of the particles have a diameter of 27 μm or lower, and wherein 50% of the particles have a diameter of about 1 μm to about 4 μm, wherein the compound is a compound of formula III, IVa, IVb, Va, or Vb:

(III)

(IVa)

(IVb)

(Va)

(Vb)

or a pharmaceutically acceptable salt thereof, wherein:
R1, R2 and R3 are independently selected from the group consisting of hydrogen, F, Cl, Br, I, —NR5R6, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —O—($C_1$-$C_6$) substituted alkyl, —O—($C_3$-$C_9$) cycloalkyl, —O—($C_3$-$C_9$) substituted cycloalkyl, aryl, heteroaryl, and heterocyclyl;
R4 is selected from the group consisting of hydrogen, —($C_1$-$C_6$) alkyl, and —$CH_2$R7;
R5 and R6 are independently selected from the group consisting of hydrogen and —($C_1$-$C_6$) alkyl;
R7 is selected from the group consisting of —O—P(=O)(OH)$_2$, —O—P(=O)(—OH)(—O—($C_1$-$C_6$) alkyl), —O—P(=O)(—O—($C_1$-$C_6$) alkyl)$_2$, —O—P(=O)(—OH) (—O—($CH_2$)-phenyl), —O—P(=O)(—O—($CH_2$)-phenyl)$_2$, a carboxylic acid group, an amino carboxylic acid group, and a peptide;
Q is selected from the group consisting of aryl, heteroaryl, —O-aryl, —S-aryl, —O-heteroaryl, and —S-heteroaryl;
X is selected from the group consisting of —($CH_2$)—, —(NR8)—, S, and O;
R8 is selected from the group consisting of hydrogen, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —C(=O)—O—($C_1$-$C_6$) alkyl, and —C(=O)—O—($C_1$-$C_6$) substituted alkyl;
Y is selected from the group consisting of —($CH_2$)— and a bond; and
m is 1 or 2,
wherein the aryl, heteroaryl, —O-aryl, —S-aryl, —O-heteroaryl, and —S-heteroaryl groups may be substituted with one or more substituents independently selected from the group consisting of F, Cl, Br, I, —NR5R6, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —O—($C_1$-$C_6$) substituted alkyl, —O—($C_3$-$C_9$) cycloalkyl, —O—($C_3$-$C_9$) substituted cycloalkyl, -aryl, -aryl-($C_1$-$C_6$) alkyl, -aryl- ($C_1$-$C_6$) alkyl, —O-aryl, —O—($C_1$-$C_4$) alkyl aryl, heteroaryl, heterocyclyl, —O—($C_1$-$C_4$) alkyl heterocycle, and —(S(=O)$_2$)—($C_1$-$C_6$) alkyl.

2. The composition of claim 1, wherein 90% of the particles have a diameter of 17 μm or lower.

3. The composition of claim 1, wherein 90% of the particles have a diameter of about 4 μm to about 10 μm.

4. The composition of claim 1, wherein 50% of the particles have a diameter of 7 μm or lower.

5. The composition of claim 1, wherein the composition comprises less than 0.1% surfactant.

6. The composition of claim 1, wherein the compound has a solubility of 0 to 3.5 μg/mL in water at 37° C.

7. The composition of claim 1, wherein the compound is (−)-trans-3-(5,6-dihydro-4H-pyrrolo[3,2,1-ij]quinolin-1-yl)-4-(1H-indol-3-yl)pyrrolidine-2,5-dione or a pharmaceutically acceptable salt thereof.

8. The composition of claim 1, further comprising an additive.

9. The composition of claim 8, wherein the additive is a diluent, disintegrant, binder, lubricant, stabilizer, or corrective.

10. The composition of claim 9, wherein the diluent is a sugar derivative, a starch derivative or a cellulose derivative.

11. The composition of claim 10, wherein the diluent is a lactose.

12. The composition of claim 1, further comprising a coating agent.

13. The composition of claim 12, wherein the coating agent is a sugar coating base agent, water-soluble film coating base agent, enteric film coating base agent, or sustained-release film coating base agent.

14. The composition of claim 12, wherein the coating agent can further comprise a plasticizer, diluent, lubricant, masking agent, colorant, gloss agent, or antiseptic.

15. The composition of claim 1, comprising about 10% to about 60% of the compound by weight.

16. The composition of claim 1, comprising about 30% to about 50% of the compound by weight.

* * * * *